US006183994B1

(12) United States Patent
Nilsson

(10) Patent No.: US 6,183,994 B1
(45) Date of Patent: *Feb. 6, 2001

(54) N-CONTAINING SACCHARIDES AND METHOD FOR THE SYNTHESIS OF N-CONTAINING SACCHARIDES FROM AMINO-DEOXY-DISACCHARIDES AND AMINO-DEOXY-OLIGOSACCHARIDES

(75) Inventor: Kurt G. I. Nilsson, Lund (SE)

(73) Assignee: Bioflexin AB, Lund (SE)

( * ) Notice: Under 35 U.S.C. 154(b), the term of this patent shall be extended for 0 days.

This patent is subject to a terminal disclaimer.

(21) Appl. No.: 09/318,263

(22) Filed: May 25, 1999

Related U.S. Application Data

(63) Continuation-in-part of application No. 08/474,464, filed on Jun. 7, 1995, now Pat. No. 5,856,143, and a continuation-in-part of application No. 08/474,173, filed on Jun. 7, 1995, now Pat. No. 5,936,075, which is a continuation of application No. PCT/SE94/00461, filed on May 17, 1994.

(30) Foreign Application Priority Data

May 17, 1993 (SE) .................................................. 9301677

(51) Int. Cl.⁷ ............................ C12P 19/26; C12P 19/60; C07H 15/00
(52) U.S. Cl. ............................ 435/75; 435/84; 536/17.2; 536/17.4; 536/17.5; 536/17.6
(58) Field of Search ....................... 425/75, 84; 536/17.2, 536/17.4, 17.5, 17.6

(56) References Cited

U.S. PATENT DOCUMENTS

| | | |
|---|---|---|
| 4,225,672 | 9/1980 | Hall ........................................ 435/74 |
| 4,415,665 | 11/1983 | Mosbach et al. . |
| 4,918,009 | 4/1990 | Nilsson . |
| 5,006,647 | 4/1991 | Kusama et al. ........................ 536/117 |
| 5,068,186 | 11/1991 | Schlingmann et al. ................. 435/96 |
| 5,246,840 | 9/1993 | Nilsson . |
| 5,372,937 | 12/1994 | Nilsson . |
| 5,405,752 | 4/1995 | Nilsson . |
| 5,414,073 | 5/1995 | Okuyama et al. ..................... 536/18.5 |
| 5,532,147 | 7/1996 | Nilsson . |
| 5,599,694 | 2/1997 | Nilsson ................................... 435/94 |

FOREIGN PATENT DOCUMENTS

| | | |
|---|---|---|
| 0 226 563 | 6/1987 | (EP) . |
| 0 516 144 | 12/1992 | (EP) . |
| 516155 | * 12/1992 | (EP) . |
| 3-284690 | * 12/1991 | (JP) . |
| 92/22565 | * 12/1992 | (WO) . |
| WO92/22565 | 12/1992 | (WO) . |
| WO93/0316 | 2/1993 | (WO) . |

OTHER PUBLICATIONS

Martin et al., Carbohydrate Research, vol. 162, pp. 181–197 (1987).

Paulsen et. al., Angewandte Chemie, vol. 21(3), pp. 155–224 (Mar. 1982).

Hindsgaul et. al., J. Biol. Chem. vol. 226(27), pp. 17858–812, (Sep. 1991).

Toone et al., Tetrahedron, vol. 45 (17), pp. 5365–5422 (1981).

U.S. application No. 08/356229, Nilsson et al., filed on Dec. 19, 1994.

U.S. application No. 08/356229, filed Dec. 19, 1994, pending.

U.S. application No. 08/424454, Nilsson, filed Apr. 27, 1995.

U.S. application No. 08/424454, filed Apr. 27, pending.

U.S. application No. 08/476110, Nilsson, filed Jun. 7, 1995.

U.S. application No. 08/476110, filed Jun. 7, 1995, pending.

U.S. application No. 08/507781, Nilsson, filed Jul. 26, 1995.

U.S. application No. 08/507781, filed Jul. 26, 1995, pending.

U.S. application Np. 08/553328, Nilsson, filed Nov. 16, 1995.

U.S. application No. 08/553328, filed Nov. 16, 1995, pending.

* cited by examiner

Primary Examiner—Kathleen K. Fonda
(74) Attorney, Agent, or Firm—Smith Gambrell & Russell, LLP

(57) ABSTRACT

Synthesis of an amino-disaccharide, amino-oligosaccharide or a derivative thereof, characterized in that a monosaccharide, a disaccharide, an oligosaccharide, a glycoside or a derivative thereof, in the presence of a glycosidase as catalyst, is reacted with an amino-deoxy-saccharide or a glycoside or derivative thereof, and that the amino-saccharide is optionally isolated from the product mixture directly or after chemical/enzymatic modification.

32 Claims, No Drawings

N-CONTAINING SACCHARIDES AND METHOD FOR THE SYNTHESIS OF N-CONTAINING SACCHARIDES FROM AMINO-DEOXY-DISACCHARIDES AND AMINO-DEOXY-OLIGOSACCHARIDES

REFERENCE TO A RELATED APPLICATION

This application is a continuation-in-part of U.S. application Ser. No. 08/474,464 filed Jun. 7, 1995, now U.S. Pat. No. 5,856,143, and is a continuation-in-part of U.S. application Ser. No. 08/474,173 filed Jun. 7, 1995, now U.S. Pat. No. 5,936,075, which is a continuation of international application PCT/SE94/00461, filed May 17, 1994 claiming priority upon Swedish application 9301677-2 filed May 17, 1993. All applications are incorporated herein by reference in their entirety.

INTRODUCTION AND BACKGROUND

The present invention describes a new method for synthesis of an amino-deoxy-disaccharide or an amino-deoxy-oligosaccharide and N-containing saccharides.

It has been found that the oligosaccharide part of various glycoconjugates (especially glycolipids and glycoproteins) have a number of important functions in vivo (Biology of Carbohydrates, vol. 2, Ginsburg et al., Wiley, New York, 1984; The Glycoconjugates, vol. I–V, Academic Press, New York; S. Hakomori, Ann. Rev. Biochem., vol 50, pp. 733–64; Feizi, Nature, pp 314, 1985; S. Hakomori, Chemistry and Physics of Lipids, vol. 42, pages 209–33). Among other thing it was found that

- the carbohydrate structures are important for the stability, activity, localization, immunogenicity and degradation of glycoproteins;
- carbohydrates are antigenic determinants (for example blood group antigens);
- carbohydrates function as receptors when bound to cell surfaces for pathogens, proteins, hormones, toxins and during cell-cell interactions;
- carbohydrates are important for oncogenesis, since specific oligosaccharides have been found to be cancer-associated antigenic determinants;
- frequently, only a smaller sequence (di- or trisaccharide) of the carbohydrate part of the glycoconjugate is required for full biological activity (e.g. receptor activity).

Universities and industry are at present working intensely on developing the use of biologically active oligosaccharides within a number of different fields, such as

- novel diagnostics and blood typing reagents;
- highly specific materials for affinity chromatography;
- cell specific agglutination reagents;
- targetting of drugs;
- monoclonal antibodies, specific against e.g. cancer-associated reagents;
- therapy;
- development of a new type of therapy, as an alternative to antibiotics, based on the inhibition of the attachment of bacteria and virus on cell surfaces with specific oligosaccharides;
- stimulation of the growth of plants and protection against pathogens.

Besides the above mentioned areas, a considerable future market is envisaged for fine chemicals based on biologically active carbohydrates.

Amino-saccharides, where an —OH group in the saccharide is exchanged for an —NH$_2$ group, in several cases have a higher (or modified) biological activity than the corresponding hydroxyl- or N-acetylamino-deoxy-saccharides, e.g. in the binding to selectins important for the initiation of inflammation processes (binding of leucocytes to epithelial cells in blood vessels). The opportunity to use such saccharides therapeutically, e.g. in acute or chronic inflammatory conditions (e.g. reperfusion, injury, and septic shock) is investigated. An important component in this and in other cases is the selective synthesis of di- and oligosaccharides in sufficient quantities. The present invention describes novel techniques for synthesis of amino-saccharides and novel techniquies for synthesis N-containing saccharides from such amino-saccharides.

Amino-deoxy-di-, tri- or higher oligosaccharides which contain one or more amino —NH$_2$ groups are of high interest for food, agricultural, pharmaceutical or diagnostic applications of carbohydrates, to modify the metabolism of the substance and/or to increase the biological effect of the natural substance.

About ten different monosaccharides are included in the carbohydrate part of the glycoconjugates: D-glucose (Glc), D-galactose (Gal), N-acetyl-D-glucosamine (GlcNAc), N-acetyl-D-neuraminic acid (Neu5Ac), D-mannose (Man), L-fucose (Fuc), N-acetyl-D-galactosamine (GalNAc), xylose (xyl), and arabinose (Ara) (the abbreviations in brackets are according to IUPAC-IUB's abridged terminology for monosaccharides, J.Biol.Chem. (1982), vol. 257, pages 3347–3354, in which publication one also can find the nomenclature used in this text to describe oligosaccharide sequences). The number of possible structures will be almost infinitely great because both the anomeric configuration and the position of the O-glycosidic bond can be varied.

The organic chemical techniques used today for synthesis of these oligosaccharide structures require an extensive protective group chemistry with many steps of synthesis and expensive catalysts (see e.g. Binkley: Modern Carbohydrate Chemistry, Marcel Dekker, New York, 1988, with references). Low total yields are obtained in these complicated reaction schemes and the technique is not favorable, especially for larger scale work.

Selective chemical synthesis of amino group containing carbohydrates and derivatives require advanced protection group chemistry with many synthetic steps. (see e.g. Binkley: Modern Carbohydrate Chemistry, Marcel Dekker, New York, 1988, with references). Efficient techniques for preparation of such carbohydrates and derivatives thereof are thus desired.

The present invention describes a process which makes possible a drastically simplified synthesis of derivatised or unmodified di-, tri-, and higher oligosaccharides which contain at least one —NH$_2$ (amino) group, and a process for the synthesis of N-containing saccharides from such derivatised or unmodified di-, tri-, and higher oligosaccharides which contain at least one —NH$_2$ (amino) group. Carbohydrate amino derivatives which required several reaction steps to synthesis with previous methods, can, with the method according to the present invention, now be obtained with only one reaction step and with absolute stereospecificity.

Enzymes are nature's own catalysts with many attractive characteristics, such as higher stereo-, regio-, and substrate selectivity as well as high catalytic activity under mild conditions. Today, great hopes are therefore placed in being able to utilize enzymes for large-scale selective synthesis of oligosaccharides with fewer reaction steps and consequently higher total yields than by organic chemical methodology.

Both hydrolases (glycosidases, EC 3.2) and glycosyltranferases (EC 2.4) can be used for synthesis (glycosidases: see Nisisawa et al, in "The Carbohydrates, Chemistry and Biochemistry", 2nd Ed., vol. IIA, pages 242–290, Academic Press, New York, 1970). With glycosidases, reversed hydrolysis (equilibrium reaction) or tranglycosylation (kinetic reaction) are often used to obtain synthesis (see e.g. K. G. I. Nilsson, Carbohydr. Res. (1987), vol. 167, pages 95–103; Trends in Biochemistry (1988), vol. 6, pages 256–264).

Reversed hydrolysis:

Transglycosylation:

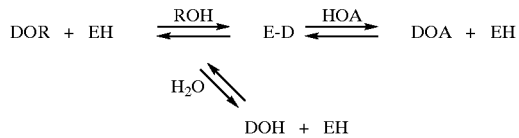

(DOH is donor saccharide, DOR is donor glycoside with α- or β-glycosidically bound aglycon (—R), HOA is acceptor saccharide and EH is enzyme).

With transferases, a nucleotide sugar (non-limiting examples are UDP-Gal, CMP-Sia, UDP-GalNAc, GDP-Fuc, etc), which is relatively expensive, is used as donor. Furthermore, glycosidases are abundant and can often be used directly without purification.

The synthetic method according to the invention includes at least one process characterized by that a glycosidase (EC 3.2) is used to catalyze an equilibrium or a transglycosylation reaction between an acceptor substance, which consists of a mono-, di-, tri- or higher oligosaccharide which contains at least one amino-deoxy group

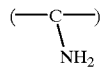

and which is modified or unmodified, and a glycosyl donor, which is a monsaccharide, disaccharide, oligosaccharide or a glycoside or derivative thereof, and that the product is used for continued synthesis and/or is isolated from the product mixture.

In this way one obtains, according to the invention, stereospecific synthesis of di-, tri-, or higher amino-deoxyoligosaccharides or derivatives thereof, which can be used directly, or after further synthesis, for a number of various applications, e.g. for pharmaceutical/medical/diagnostical studies, for applications in therapy or diagnostics, as additives in cosmetics or in food, for modification of separation material, affinity chromatography, modification of amino acids, peptides, proteins, fatty acids, lipids, enzymes, or recombinant proteins.

In the synthesis according to the invention, the capacity of glycosidases to form stereospecific glycosidic linkages between a glycosyl donor (DR in the scheme below, where D symbolizes the transferred carbohydrate part) and a glycosyl acceptor (HOA), summarized in the scheme below:

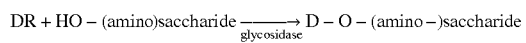

The reaction according to the invention can be carried out according to two principles, either with equilibrium controlled synthesis (R=H), or with transglycosylation reaction (R=F, or an organic group; kinetically controlled reaction). These general types of reactions are well know to the expert and their carrying out, as well as the choice of glycosyl donor and glycosidase, do not restrict the scope of the invention.

Nitrogen-containing saccharides, e.g. of the type illustrated in the figures below are of interest in several connections.

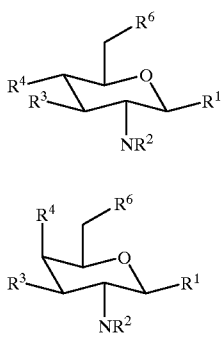

in which I symbolizes a derivatized 2-amino-2-deoxy-D-glucopyranoside (derivatized GlcN) and II symbolizes a derivatized 2-amino-2-deoxy-D-galactopyranoside (derivatized GalN) and R symbolizes hydroxyl groups or organic or inorganic groups (e.g. $-NR^2=NH_2$ or —NHAc group) and in which at least one of $R^1$, $R^3$, $R^4$ or $R^6$ is constituted by a mono-, di-, tri- or higher oligosaccharide group which is glycosidically bound to I or II and is, for the rest, non-derivatized or is derivatized with one or more organic or inorganic groups (as defined above). Examples of such saccharides are Lewis-a, Galβ1–3 (Fucα1–4)GlcNAc and Lewis-x blood-group structures and derivatives thereof and of other biologically active oligosaccharides in which the oligosaccharide derivative is defined here and below in that the saccharides are substituted as Lewis-a or Lewis-x in at least one hydroxyl group and/or in amino-deoxy position with an organic (e.g. an aliphatic, aromatic group or a saccharide group) or inorganic group (sulfate, carboxyl, phosphate group, for example).

Examples of other saccharides are saccharides containing at least one of an α- or β-glycosidically linked sialyl-, D-xylosyl-, D-mannosyl-, N-acetyl-D-glucosaminyl-, N-acetyl-D-galactosaminyl- or D-glucosyl- group.

These and other derivatized 2-amino-2-deoxy-saccharides (derivatized ManN) have several interesting biological applications.

SUMMARY OF THE INVENTION

Synthesis of an amino-disaccharide, amino-oligosaccharide or a derivative thereof, characterized in that a monosaccharide, a disaccharide, an oligosaccharide, a glycoside or a derivative thereof, in the presence of a glycosidase as catalyst, is reacted with an amino-deoxy-saccharide or a derivative thereof, and that the amino-saccharide is isolated from the product mixture directly or after chemical/enzymatic modification. Synthesis of N-containing saccharides from such amion-saccharides.

DETAILED DESCRIPTION OF THE INVENTION

The synthesis, according to the invention, is carried out by reacting a monosaccharide, a disaccharide, an oligosaccharide, a glycoside or a derivative thereof with an amino-deoxy-saccharide or a derivative thereof in the presence of a glycosidase (EC 3.2) as a catalyst.

As nonlimiting examples of amino-deoxy-monosaccharides which can be used as acceptors one can mention a 2-amino-2-deoxy-glucopyranoside, a 2-amino-2-deoxy-galactopyranoside, or a 2-amino-2-deoxy-mannopyranoside (thus, in the scheme below, $R_3$, $R_4$ and $R_6$ are —OH and $R_1$ is one of e.g. pentenyl-, —SEt, —SPh, —OEtBr, —OEtSiMe$_3$, —OAll, —OPh, —OCH$_2$Ph, or —OR, where R is e.g. CH$_3$(CH$_2$)n; n is an integer, preferably in the range 0–12; or where R is for example an amino acid residue, peptide residue, or a derivative thereof):

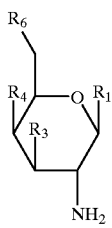 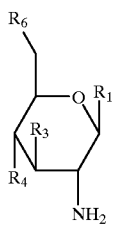

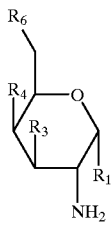 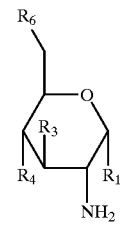

Other nonlimiting examples of amino-deoxy-saccharides is an 2, 3, 4, 5 or 6 amino-monosaccharide as above, which has been derivatised in one or two of the positions 2, 3, 4, 5 or 6. As examples of such derivatives one can mention derivatives in which one or two of the hydroxyl groups have been modified to an allyloxy- (CH$_2$=CH—CH$_2$O—), bensyloxy- (PhCH$_2$O—), bensoyloxy- (PhCOO—), chloroacetyloxy- (ClCH$_2$COO), p-methoxybensyloxy- (p-MeO—PhCH$_2$O—), trityl- (Ph$_3$C0-), trialkylsilyloxy-, tosylate-, mesylate-, phosphate-, sulfate-, carboxylate, esters such as RCOO— where R is CH$_3$(CH$_2$)$_n$ (n=1–20) or a pivaloyloxy-group or derivatives in which two vicinal hydroxyl groups have been modified e.g. bensylidene acetal, isopropylidene ketal or an ortho ester, pivaloyl-group, tetrahydropyranyl, (2-methoxyethoxy) methylisopropylidene ketal, cyclohexylidene ketal, benzylidene acetal, orthoester, —ONO$_3$, derivative of sulfate-, phosphate-, carboxylate, esters i.e. of the type —OC(O)R as acetyl-, butanoyl-, octanoyl-, benzoyl-, pivaloyl-, etc. The structures below, modified in a similar way, can also be used as acceptor substances in the method according to the invention.

If modified amino monosaccharide is used, the choice of the type of modification of the acceptor is decided by what is desired in the specific situation and the literature is rich in information on protection groups/modification of carbohydrates and carbohydrate synthesis in general (e.g. "Modern Carbohydrate Chemistry", Binkley, Marcel Dekker, 1988 with references; Paulsen, Chem. Soc. Rev., vol. 13, pages 15–45). Below are a few examples of acceptor substance categories which can be used according to the invention but which in no way are meant to restrict the scope of the invention.

Similarly, modified amino di, tri- or higher oligosaccharides can also be used as acceptors.

I.
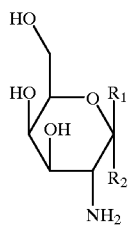

II.
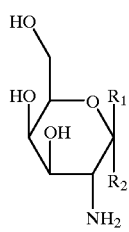

III.
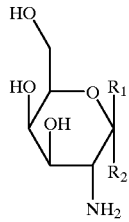

IV.
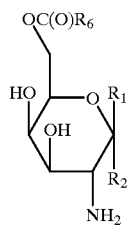

V.
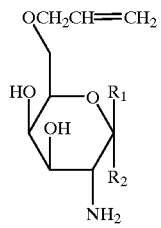

VI.
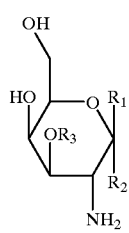

VII.
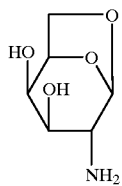

VIII.
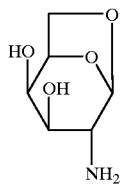

IX.
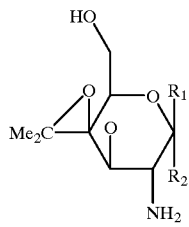

X.
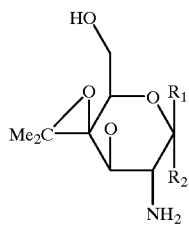

XI.
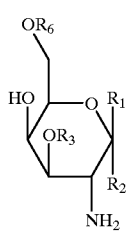
$R_1$ or $R_2$ = H

XII.
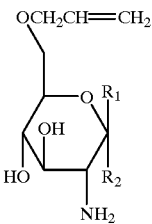

XIII.
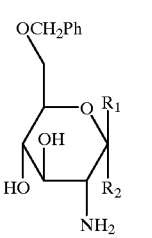

XV.
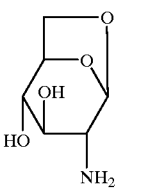

XVI.
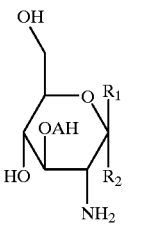

XVII.
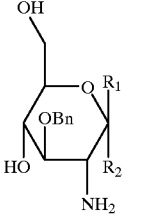

In the structures I–XI above, $R_3$ is for example an alkyl, allyl, benzyl, chlorobensyl, benzoyl-group or another type of suitable protection group for the specific synthesis. $R_6$ can be aromatic group such as Ph— or an alkyl group (e.g. propyl- or $(CH_3)_3$-group). In the structures XII–XVII, $R_3$ is for example an acetyl-, phenoxyacetyl-, methoxyacetyl- or an chlorometoxyacetyl group. $R_6$ can be an aromatic group, such as Ph— or an alkyl group (e.g. propyl- or $(CH_3)_3$ group). If $R_2$ for example is H, then $R_1$ is one of the groups which has been mentioned for $R_1$ above, and vice versa if $R_1$ instead is H. Similarly, position 4 can be modified instead of position 3 or 6 in the examples above, and other positions than the 2 position may be modified with an amino-deoxy group.

As an example to illustrate the invention, but which in no way is meant to limit the scope of the invention, can be mentioned that if, for example, α-galactosidase is used as enzyme and 2-amino-2-deoxy α-D-galactopyranoside is used as acceptor substance, and if, for example raffinose, methyl α-D-galactopyranoside, GalαF (F=fluoro) (or p-nitrophenyl) α-D-galactopyranoside is used as glycosyl donor (transglycosylation reaction), an α-glycosidically linked 2-amino-2-deoxy-digalatosyl derivative of the type

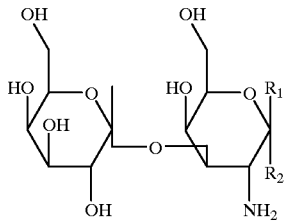

i.e. a 2-NH$_2$-2-deoxy-derivative of Galα1–3Galα-R, is obtained. As another example, if I is used as acceptor and a α-galactosaminidase, and e.g. (GalNAcα-OPh, GalNAcαF or GalNAcα-OPhNo$_2$—P, is used as glycosyl donor, a 2-O-derivative of GalNAcα1–3Galα-R is obtained.

The products can be used if desired for further synthesis, e.g. of higher oligosaccharide with chemical synthesis and the literature is extensive on how to use such partially protected carbohydrates (see references in Binkley and Paulsen mentioned above).

If a β-galactosidase is used instead of an α-galactosidase and if lactose, or for example p-nitrophenyl-β-D-galactopyranoside, is used as glycosyl donor, and if 2-amino-2-deoxy-glucose or a derivative thereof (see e.g. XII–XVII above) is used as acceptor, β-bound derivatives of Gal-GlcNH$_2$ or Gal-GlcNH$_2$—R are obtained. Examples of partially protected Gal-GlcNH$_2$ or Gal-GlcNH$_2$—R derivatives, which can be used e.g. for synthesis of Lewis-x or Lewis-a trisaccharide structures (or which can be used for further synthesis of disaccharide derivatives of these) are given below:

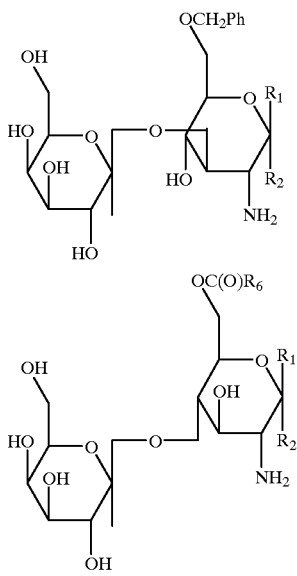

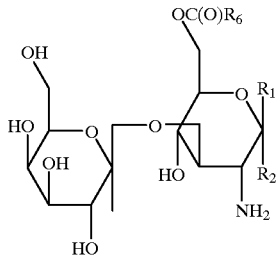

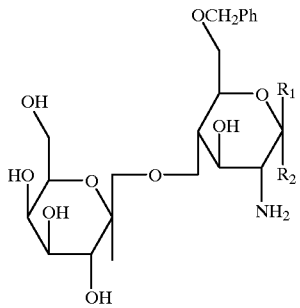

Moreover, if instead an α-L-fucosidase is used with, for example, nitrophenyl α-L-fucopyranoside or with Fucα-F as glycosyl donor, one can synthesis the corresponding derivatives of e.g. α-bound Fuc-Gal-NH$_2$—R and of α-bound Fuc-GlcNH$_2$—R with the method according to the invention, similarly with N-acetyl-β-glucosaminidase or N-acetyl-β-galactosaminidase one can prepare derivatives of β-bound GlcNAc-Gal-NH$_2$ and GlcNAc-GlcNH$_2$ or GalNAc-Gal-NH$_2$ and GalNAc-GlcNH$_2$, respectively, with β-glycosides of GlcNAc and GalNAc, respectively, as glycosyl donors. Similarly, α-sialidase can be used to catalyze synthesis of e.g. sialylated 2-amino-2-deoxy-galactose (Neu5Acα-GalNH$_2$) or of 2-amino-2-deoxy-galactosamine-derivatives (derivatives of Neu5Acα-GalNH$_2$) by employing e.g. nitrophenyl glycoside of N-acetylneuraminic acid and a partially protected 2-amino-2-deoxy-galactose derivative, respectively, as acceptor.

If an endoglycosidase is used, one can prepare longer oligosaccharide derivatives with the method according to the invention. Then, the donor substance is of the type disaccharide, tri- or higher oligosaccharide or a glycoside, e.g. nitrophenyl glycoside of any of these. Similarly, any of the R groups of the acceptor substance might be a saccharide unit.

The reaction above can also be carried out as equilibrium reactions with monosaccharides as glycosyl donors.

The benzyl- or the allyl group (or other groups mentioned in connection with the figures above) in the products above, can easily be chemically changed by the expert to a wide range of groups, and in this way selective synthesis of different amino-deoxy-disaccharide derivatives (e.g. O-phosphate, O-sulfate, etc) or higher amino-deoxy-oligosaccharides can be selectively synthesized according to the invention.

The substrates are selected with regard to the oligosaccharide which is to be synthesized, and are often commercially available or can by synthesized by organic or enzymatic methods and therefore do not restrict the use of the invention. The donor substrates which are used according to the invention are of the same type which have been used in previous transglycosylation reactions (see for example the articles by K. G. I. Nusson in Carbohydrate Res. vol. 167 and in Trends in Biotechnology, vol. 6 as noted above).

As further examples of acceptor substances which can be used with the method according to the invention can be mentioned amino-deoxy di- or oligosaccharides (or glycosides thereof) in which the carbohydrate part contains one or more of the following monosaccharides: D-glucose, D-galactose, D-mannose, N-acetyl-neuraminic acid, N-acetyl-D-galactosamine, N-acetyl-D-glucosamine and L-fucose, or analogs of these. When the acceptor substance is a glycoside, the aglycone can be a glycosidically bound (α- or β-configuration) aliphatic or aromatic compound (as for example methyl, ethyl, 2-bromoethyl, $(CH_2)_n COOMe$, n>1, allyl or other substances that can be polymerized, benzyl, pentenyl, trimethylsilylethyl, amino acids, derivatives thereof, peptides, derivatives thereof, nitrophenyl, etc).

Other types of aglycons of special interest are amino acids (serine, threonine, hydroxyproline, hydroxylysine, asparagine, etc), peptides, lipids and derivatives or analogs to substances within these three groups. The amino acid and peptide glycosides can be protected on their amino and/or carboxyl groups with the common protecting groups used in peptide synthesis (FMOC, CBZ, BOC, etc). By using usch aglycones fragments or analogs of glycoconjugates can be synthesized according to the invention; the terms aglycones, fragments and analogs are terms well known to those skilled in the art. Moveover, the aglycon can be an amino, nitrile, or an amido group or a fluorogenic substance, or may contain a phosphate, sulfate, or carboxyl group or a derivative thereof. Another important type of amino-deoxy saccharide derivatives consists of substances where the ring oxygen (i.e. the C-5 oxygen of hexoses), has been replaced by sulfur, nitrogen, etc. The glucose analog moranoline, where the C-5 oxygen has been replaced by nitrogen, is an example of such a derivative. Oligosaccharide analogs that are efficient inhibitors against enzymes or carbohydrate binding proteins may in this manner be synthesized according to the invention.

The donor substances which can be used with the method according to the invention are the same as those employed in previous methods involving enzymatic transglycosylations (see references above) and thus do not limit the scope of the invention.

As examples of donor substances that can be used with the method according to the invention may be mentioned monosaccharide glycosides and di- or oligosaccharides (or gylcosides thereof) in which the carbohydrate part contains one or more of the monosaccharides D-galactose, D-glucose, D-mannose, N-acetyl-neuraminic acid, N-acetyl-D-galactosamin, N-acetyl-D-glucosamin and L-fucose. As examples of suitable glycosyl donors may be mentioned the nitrophenyl α- or β-glycosides of the monosaccharides above, lactose, dimannose and raffinose. As examples of suitable donor substances for endoglycosidases may be mentioned nitrophenyl derivatives of biologically active carbohydrate sequences (e.g. Galβ1–3GlcNAcβ-OPhNO$_2$-p), biologically active oligosaccharides or structures of the type Glc(β1–3Glc)$_n$β1–3Glc (n>1).

The concentration of the glycosyl donor in the reaction mixture is selected with regard to the oligosaccharide which is to be synthesized and also with regard to the properties of the enzyme and therefore do not restrict the use of the invention. In some cases, addition of the donor in smaller portions may be advantageous in order to minimize the risk that the donor also acts as an acceptor (unless this is desired).

The enzymes are selected primarily with regard to which oligosaccharide is to be synthesized. The enzyme may be used in situ or after partial or complete purification from their natural environment. The enzyme may be used in soluble form or immobilized to a solid support by e.g. adsorption, encapsulation, chelation, precipitation or covalent binding.

Examples of α- and β-glycosidases which may be used according to the invention are D-mannosidases, D-galactosidases, L-fucosidases, N-acetyl-D-galactosaminidases, sialidases, hexosaminidases and other glycosidases of EC group 3.2 (Enzyme Nomenclature, Academic Press, 1984). Both endo- and exoglycosidases may be used in the method according to the invention.

The degree of purity of the enzyme employed is not critical. The enzyme may be used in situ or after complete or partial isolation from it natural biological environment. Also, a crude extract of the organism or a tissue thereof may be used. The enzyme may also have been obtained after precipitation with e.g. ammonium sulfate. The enzyme may be present in crystalline form or be enclosed within micelles. The biochemical literature is rich in detailed information about the purification and isolation of glycosidases. The enzyme may be produced with recombinant techniques. Then, if desired, one or more of the amino acids in the amino acid sequence of the enzyme may be changed in order to optimize the properties of the enzyme, e.g. themostability, catalytic efficiency and/or regioselectivity.

The enzyme may be used in soluble form or may be immobilized by e.g. adsorption, encapsulation, chelation, precipitation or covalent binding to a solid support, such as a polymeric substance, or a derivative thereof which is insoluble in protic or aprotic solvents (Methods in Enzymology, vol. 44, Academic Press, 1976). The form selected is not critical to the invention. If the enzyme is used in soluble form, it may first have been chemically modified in a suitable manner in order to e.g. increase the thermostability or the stability in organic cosolvents. Enzyme immobilized to an insoluble polymer comprising, for example, agarose, cellulose, hydroxyethyl acrylate, glass, silica, polyacrylic amide, polyacrylate-based plastics, etc., is readily separated from the product mixture, and the enzyme may thus be reused. An additional advantage is that in many cases a certain stabilization against elevated temperatures and organic cosolvents is obtained.

Moreover, the products can be used for further enzymatic synthesis with glycosidases or glycosyltranferases. For example, α-sialyltranserase can be used to catalyze the formation of sialylated Gal-GlcNAc-derivatives and β-galactosyltransferase can be used to form oligosaccharide derivatives of the type Gal-GlcNAc-Gal-R, which then can eventually be sialylated and/or be used for further chemical synthesis, etc.

If a modified 2-amino galactoside of glucoside is used as acceptor, the choice of aglycon is made with regard to the application of the product. Aglycons of special interest are amino acids (serine, threonine, hydroxyproline, hydroxylysine, asparagine, etc.) peptides, lipids and derivatives or analogs of substances within these three groups. Amino acid or peptide glycosides can be protected on their amino- and/or carboxyl functions with common groups used in peptide synthesis (FMOC, CBZ, BOC, etc). Product obtained with modified alkyl glycosides (e.g. modified methyl-, octyl-, docecyl glycosides) as acceptor substances, may be used as inhibitors in affinity chromatography or in agglutination tests, inhibition-based therapy or for drug-targeting, as structural units for further enzymatic synthesis. Nitrophenyl glycosides can be reduced to aminophenyl glycosides. Glycosides with a polymerisable aglycon, as for example 2-hydroxyethylemethacrylate, can be used. As an example of a N-glucosidically bonded aglycon, —NHCO $(CH_2)_5NH_2$, may be mentioned. Other types of aglycons which can be used are those used e.g. in the synthesis of glycolipids/analogs for conversion to ceramides/analogs, e.g. aglycons of the type described by Magnusson et al in J. Org. Chem., 1990. Thioglycosides (e.g. SEt or SPh) can be used with the method according to the invention to produce products which are suitable for further chemical synthesis. The choice of protection group/derivative, aglycon, position of derivatized hydroxyl groups, can be used to influence the yield and regioselectivity of the reactions with the method according to the invention. Thus, for example, the use of more hydrophobic aglycons (e.g. p-metoxy-benzyl-, benzyl-, compared with e.g. allyl-) can result in a higher yield at the same acceptor concentration.

The enzymes are selected with regard to the final oligosaccharide which is to be synthesized. The enzyme can be used in situ (especially several glycosidases) or after partial or complete purification from their natural environment. The enzyme may be used in soluble form or immobilized to a solid phase by e.g. adsorption, encapsulation, chelation, precipitation or covalent binding. Simultaneous use of glycosidase and glycosyltransferase in soluble form or immobilized to a solid phase (eventually co-immobilized) may be advantageous according to the invention in facilitating the conversion of the intermediate oligosaccharide product to the final product oligosaccharide. In this way the method according to the invention gives important advantages compared to previous methods: purification of intermediary product is not necessary, secondary hydrolysis is minimized (i.e. higher yield), and trisaccharides or higher oligosaccharides can be synthesized in a minimum of "pots" (in some cases one-pot reactions). This is facilitated by the high acceptor specificity of most glycosyltransferases: the transferase does not react with the wrong isomer.

The synthetic procedure according to the invention can be carried out under highly diverse conditions as regards, for example, pH, type of buffer, temperature and concentration of the reactants. Various cosolvents (N,N-dimethyl formamide, acetonitrile, dimethyl sulfoxide, dioxane, pyridine, methanol, ethanol, ethylene glycol, etc) may be used and in varying concentrations together with water (0–99%). Moreover, the reactions can be carried out in two-phase systems: water-organic solvent. THe use of acceptor aminosaccharides modified with organic groups facilitates recovery of the product in the organic phase.

The reaction conditions are not critical but are selected primarily on the basis of the properties of the reactants employed in the synthesis concerned, and also on the basis of practicality. For example, it may be mentioned that it is usually convenient to use room temperature with enzymes and, in the case of water-rich medium, the pH is usually in the range 4–11. The solubility of amino-saccharides in water is increased/decreased by decreased/increased pH, and in some cases a pH below 8 and above 4 is preferably used to increase the solubility of the acceptor amino-saccharide.

Organic cosolvents may be used to minimize the hydrolytic side-reaction. For the same reason, two-phase systems may be used. Examples of cosolvents are tetrahydrofurane, acetonitrile, DMF. The choice of solvent and of the concentration or organic solvent can easily be made by the expert and does not limit the scope of the invention. Use of high concentrations of organic solvent (up to almost 100% of the total volume solvent) can be especially advantageous when acceptor derivatives with hydrophobic groups which have good solubility in organic solvents are used, e.g. acceptors modified with ester groups (e.g. acetyl-, bensoly-, butanoyl-, pivaloyl-, octanoyl-grupper, etc.) and/or with for example allyl, bensyl, trityl- or other groups. In this way relatively high concentration of the acceptor can be achieved in organic solvents and the hydrolytic side-reaction can be decreased due to the low water content. The method according to the invention allows synthesis in organic solvent of e.g. amino deoxy trisaccharde derivatives and higher oligosaccharide derivatives with exoglycosidases by using hydrophobic protected derivatives of amino deoxy di-, tri- or oligosaccharides, which has only one or a few free dydroxyl groups, as acceptors.

To increase the solubility/availability in organic solvent and facilitate the reaction with the donor substance, one can use for example phenyl boronate, which forms a complex with saccharides with vicinal diols and the resulting donor-boronate complex has, because of the phenyl group, a higher solubility in organic solvent.

The reaction temperature may also be varied to influence product yield and the stability of the enzyme and does not restrict the scope of the invention. The temperatures most frequently used lie in the range 4°–55° C., but lower temperatures and temperatures below 0° C. can be used which can be facilitated if organic cosolvent is used. Higher temperatures can be used with thermostable glycosidases and substrates, and also with enzymes stabilized against thermal denaturation by employing, for example, high substrate concentrations (Johansson et al, Biotechnol. Lett. (1986), vol. 8, pages 421–424). An advantage with high temperatures is, for example, that high substrate concentrations may be used, which reduces the water activity and thus increases the yield of product. Another advantage is that the activity of the enzyme increases, which means shorter reaction times at increased temperatures. One additional advantage is that glycosides, e.g. methyl or ethyl glycosides, which are hydrolyzed slowly at room temperature can be used as suitable glycosyl donors at increased temperatures (50°–60° C.). The upper temperature limit is determined by the thermostability of the enzyme in the reaction medium. For some transglycosidations, a lower temperature was found to give a higher yield of product glycoside.

The concentration of the acceptor is a parameter which can be used to influence the yield of the reactions according to invention. High concentrations are preferrable in both equilibrium and transglycosylation reactions to mimimize hydrolytic side-reactions, which usually means that depending on the solubility of the acceptor, ca 0.05–7 M concentration of acceptor is used. A high concentration of donor is often used and especially in equilibrium reactions. In general, high concentrations of substrates are obtained by heating the reaction mixture to near the boiling point for a few minutes, allowing the solution to cool to the reaction temperature (usually 4°–75° C., depending on the temperature for optimum yield and thermostability of the enzyme/substrate and then add the enzyme. Cosolvents can be used to increase the solubility of substrates with hydrophobic groups.

The reaction can be monitored by means of TLC, HPLC, or by spectrophotometric measurement of liberated aglycon (e.g. p-nitrophenol, 400 nm). Charring of TLC-plates with ninhydrin may be used for detection of $NH_2$-groups. When a desirable yield of the product has been obtained, the reaction is terminated by denaturation of the enzyme by changing the pH, increasing the temperature and/or adding organic cosolvent (such as ethanol). Heating to 60°–85° C. for 3–5 min (eventually followed by addition of ethanol to a concentration of about 80%) is usually sufficient.

Various techniques may be used for isolation of the product. Precipitation from the water-phase or from an organic solvent (such as e.g. ethanol, methanol, ethyl acetate) is useful, especially when an excess of one of the reactants is used or when the donor, acceptor or products have different solubilities. After the equilibrium controlled synthesis or the transglycosylation reaction and after e.g. heat treatment as above and dilution of the reaction mixture, it can be useful to add a second glycosidase, which has a different regioselectivity than the glycosidase used in the synthesis. In this way, any unwanted regioisomers (for example with 1–6 linkages) may be more or less selectively hydrolyzed, which facilitates isolation of the desired product.

Precipitation, extraction of the water phase with an organic solvent, and hydrolysis of byproducts are complementary to chromatography (ion exchange chromatography, gel filtration, HPLC with, for example, amino-silica, reversed phase silica or the new Dionex columns).

Some examples of how the invention can be used in practice, but which by no means are meant to restrict the scope of the invention, are given below.

Examples of substances, which can be used as donor saccharides (DR, where D is the transferred glycosyl group in the reaction) according to the invention is D-glycose, D-mannose, L-fucose, D-galactose, xylose, N-acetyl-D-glucosamine, N-acetyl-D-galactosamine, N-acetyl-neuraminic acid, glycosides of these, disaccharides or oligosaccharides containing one or more of the monosaccharides above (e.g. lactose, raffinose, chitobiose), and derivatives of any of the substances mentioned above, e.g. modified in one or more of the ring hydroxyl groups.

The reaction according to the invention can therefore be summarized as follows:

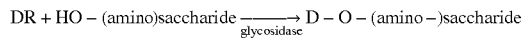

where D is glucosidically bound to the saccharide unit of the amino-saccharide. Endo- or exoglycosidase (EC group 3.2) are used as enzyme, and the reaction is carried out as a transglycosylation reaction. The equilibrium type reaction may also be chosen Non-limited examples of exoglycosidases are α-galactosidase, β-galactosidase, β-N-acetyl-glucosaminidase, β-N-acetyl-galactosaminidase, α-L-fucosidase, α-sialidase, α- or β-xylosidase, α-mannosidase or β-mannosidase.

The reaction conditions are chosen according to the reaction; some non-limiting examples are given below: The concentration of reactants are usually in the interval 0.05 M to above 1 M depending on the solubility of the reactants, the temperature is usually in the range 0° to 80° C. and the reaction is usually carried out in buffered water, pH 4–9; the pH and temperature are chosen according to e.g. the enzyme's properties, eventually an organic co-solvent can be used (1–99% of e.g. tetrahydrofurane or acetonitrile). The reaction is usually stopped when the maximum yield of amino-saccharide product has been obtained and the product is isolated with, for example, one or more of column chromatography (adsorbent for example ion-exchange material, Sephadex or silica), extraction, precipitation, crystallization and/or filtration techniques.

EXAMPLES

As a non-limiting specific example one can mention the production of thioetyl β-D-galactopyranosyl-(6-bensyl-2-amino-2-deoxy)-β-D-glucopyranoside produced via reaction between nitrophenyl β-D-galactopyranoside and thioetyl (6-bensyl-2-amino-2-deoxy)-β-D-glucopyranoside in e.g. sodium acetate buffer, pH 5, catalyzed by β-galactosidase.

The product can be used either directly e.g. in biological/medical applications or can be used as a synthetic intermediate for further synthesis of higher oligosaccharides or other derivatives.

Synthesis of derivatives of Galβ1-3GlcNH$_2$ and Galβ1-4GlcNH$_2$ respectively (constituents of Lewis-blood group substances, such as Lewis-a, Lewis-x and sialylated structures): By using for example derivatised glycoside of glucosamine, such as e.g. structures XIII or XIV, as acceptor dissolved in for example (1/1 V/V) tetrahydrofurane:sodium acetate buffer (pH 5.5, 0.05 M), Galβ-OPpNO$_2$-0 as donor, and β-galactosidase as catalyst, structures of the types below can be obtained:

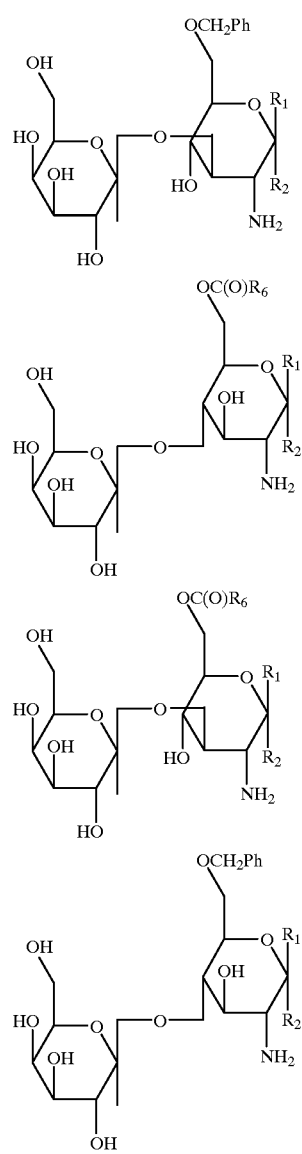

Such structures can be used directly in various applications, or can be used for further chemical or enzymatic synthesis. The galactosyl moiety can for example be modified with chemical or enzymatic methods (lipase or galactose oxidase, followed by chemical modification) leaving one free hydroxyl group in the glucosaminyl-moiety, which can be modified with for example a fucosyl group.

Similarly, by using an acceptor of the type below, the corresponding β-bound 3-O-protected Gal-GlcNH$_2$-derivative can be obtained.

After protection of the free hydroxyl groups and the amino group in the product and deprotection of the 3-O-position can, for example, an α-bound L-focosyl group can be introduced, which gives the modified Lewis-x structure, which can be, for example, sialylated to give e.g. NeuAcα2-3Galβ1-4(Fucα1-3)GlcNR$_2$-R. In an analogous way, one can produce regioisomers, such as Galβ1-3(Fucα1-4) GlcNR$_2$-R, and analogs/derivatives of Lewis-x, Lewis-a, and of sialylated Lewis-substances.

Example 1

A non-limiting example of the application of the method according to the invention is the synthesis of Galβ1-3(6-O-Bn)GlcNH$_2$βSEt employing thioethyl (6-O-bensyl-2-amino-2-deoxy)-β-D-glucopyranosid, abbreviated (6-O-Bn) GlcNH$_2$βSEt, as acceptor and galactose or lactose or a galactoside, e.g. nitrophenyl α-D-galactopyranoside as glycosyl donor and β-galactosidase from ox testes as catalyst.

Other sources of β-galactosidase which gives the linkage may be used according to the invention. The reaction was carried out at room temperature with initial concentration of substrates typically in the range of 0.06 M to 0.3 M. The donor was used in excess over the acceptor. A crude ammonium sulfate precipitate of the enzyme was used in the reaction, which was carried out at pH 5 in 0.05 M sodium acetate buffer. The reaction was terminated by heat treatment for ca 5 minutes in a boiling water bath. The product was isolated by e.g. adjusting the pH ot ca 10.5 (minimizing the charge on the amino group), extraction of the water phase with ethyl acetate, followed by butanol extraction, the butanol phase was evaporated and the residue dissolved in water and applied to an ion-exchanger (in this example a sulphopropyl group containing fast-flow ion-exchanger from Pharmacia). The fractions containing the product was evaporated and the product dried and analyzed by NMR.

Similarly, another 6-O-substituted product than the bensyl-substituted product and/or another type of 1-substituted derivative than the 1-thioethyl substituted product, can be obtained by instead of (6-O-Bn) GlcNH$_2$βSEt employing another 6-O- and/or 1-substituted acceptor as exemplified in the description.

Another non-limiting example is the synthesis of Fucα1-4 (6-O-Bn)GlcNH$_2$βSEt using thioethyl (6-O-bensyl-2-amino-2-deoxy)-β-D-glucopyranoside, abbreviated (6-O-Bn)GlcNH$_2$βSEt, as acceptor and focose or a fucopyranoside, e.g. nitrophenyl α-L-fucopyranoside as glycosyl donor and α-L-fucosidase from ox kidney as catalyst.

The reactions above can for example be carried out with ca 0.1 M concentrations of substrate and the isolation can be carried out by the use of an ion changer (e.g. sulphopropyl-containing material) and extraction of the water phase with a suitable solvent, e.g. butanol or ethylacetate.

The two substances above are of interest for example as inhibitors/modifiers of selectin-carbohydrate interactions in vivo such as in different inflammatory reactions e.g. septic chock, rheumatism and asthma, but also as inhibitors/modifiers of the up-regulation of IgE-synthesis in vivo (for example inhibition, modification of the FceRll-CR interaction, see e.g. Nature (1993), volume 366, page 41–48, and references therein, for an overview).

One of the advantages with the method according to the invention, is that the amino-disaccharide- or the amino-oligosaccharide product and derivatives thereof can be synthesized directly, and thus no modification of the amino-group is required after the glycosidase-catalysed reaction. Another advantage is that partially modified amino-sugar derivatives can be produced stereospecifically and under reaction specific conditions. Such derivatives can be used directly in various applications or an synthetic intermediates for further synthesis of higher oligosaccharides or other derivatives.

Example 2

Synthesis of Galβ1-4(6-O-Bn)GlcNH$_2$βSEt. The synthesis of this compound is achieved similarly as above, but another source of enzyme which gives the β1-4 linked product, is employed, e.g. a yeast enzyme such as the one from *Bullera singularis*. In this case the reaction can be carried out as a fermentation with e.g. lactose as the glycosyl donor and with intact cells.

Similarly, another 6-O-substituted product than the bensyl-substituted product and/or another type of 1-substituted derivative than the 1-thioethyl substituted product, can be obtained by instead of (6-OBn)GlcNH$_2$βSEt employing another 6-O- and/or 1-substituted acceptor as exemplified in the description.

Example 3

Synthesis of Galβ1-3GlcNH$_2$βSEt and Galβ1-3GlcNH$_2$βSEt. See example 1, similar conditions and enzyme may be used, but instead GlcNH$_2$βSEt, or GalNH$_2$βSEt to obtain the latter product, is used as the acceptor. Here, extraction is less favorable for isolation, and instead ion-exchanger as above may be used followed by e.g. precipitation or a second chromatographic step.

Example 4

Synthesis of Galβ1-4GlcNH$_2$βSEt. See example 3 for acceptor substrate and isolation. Here, the source of enzyme is used which give the 1–4 linked product (cf. example 2). If a microorganism like in example 2 above is used then a fermentation like in example 2 may be used.

Example 5

Synthesis of Galβ1-3(6-OAll)GlcNH$_2$βSEt. This compound and other 6-substituted derivatives and other 1-substituted derivatives is obtained as in example 1 above, but instead of the 6-O-bensyl aminosaccharide the 6-O-allyl- or another 6-substituted derivative and/or another type of 1-substituted derivative is used as acceptor as mentioned in the description.

Example 6

Synthesis of Galβ1-4(6-OA11)GlcNH$_2$βSEt. This compound and other 6-substituted derivatives and 1-substituted derivatives is obtained as in example 2 above employing a β-galactosidase which gives a 1–4-linked product, but instead of the 6-O-bensyl aminosaccharide the 6-O-allyl- or another 6-substituted derivative or another type of 1-substituted derivative is used as acceptor as mentioned in the description.

Example 7

Synthesis of Galβ1-3(4-OBn)GlcNH$_2$βSEt. This compound and other 4-substituted derivatives and other 1-substituted derivatives is obtained as in example 1 above employing an enzyme which gives a 1-3-linked product, but instead of the 6-O-bensyl aminosaccharide the 4-O-bensyl- or another 4-substituted derivative and/or 1-substituted derivative is used as acceptor as mentioned in the description.

Example 8

Synthesis of Galβ1-4(3-OBn)GlcNH$_2$βSEt. This compound and other 3-substituted derivatives is obtained as in example 2 above employing a β-galactosidase with gives a 1-4-linked product, but instead of the 6-O-bensyl aminosaccharide the 3-O-bensyl- or another 3-substituted derivative is used as acceptor.

Example 9

Synthesis of Fucα1-4(6-OBn)GlcNH$_2$βSEt. The reaction was carried out at room temperature with initial concentration of substrates typically in the range 0.06 M to 0.1 M. A crude ammonium sulphate precipitate of the enzyme was used in the reaction, which was carried out at pH 5 in 0.05 M sodium acetate buffer. The reaction was terminated by heat treatment for ca 5 minutes in a boiling water-bath. The product was isolated by e.g. adjusting the pH to ca 10.5 (minimizing the charge on the amino-group), extraction of the water phase with ethyl acetate, followed by butanol extraction, the butanol phase was evaporated and the residue dissolved in water and applied to an ion-exchanger (in this example a sulphopropyl group containing fast-flow ion-exchanger from Pharmacia). The fractions containing the product was evaporated and the product dried and analyzed by NMR.

Similarly, another 6-O-substituted product than the bensyl-substituted product and/or another type of 1-substituted derivative than the 1-thioethyl substituted product, can be obtained by instead of (3-OBn)GlcNH$_2$βSEt employing another 6-O- and/or 1-substituted acceptor as exemplified in the description.

Example 10

Synthesis of Fucα1-3(6-OBn)GlcNH$_2$βSEt. The synthesis of this compound is achieved similarly as above, but another source of enzyme, which gives the α1-3 linked product, is employed. Similarly, another 6-O-substituted product than the bensyl-substituted and/or another type of 1-substituted derivative than the 1-thioethyl substituted product, can be obtained by instead of (6-OBn)GlcNH$_2$βSET employing another 6-O- and/or 1-substituted acceptor.

Example 11

Synthesis of Fucα1-3(4-OBn)GlcNH$_2$βSEt. The synthesis of this compound is achieved similarly as above, but with (4-OBn)GlcNH$_2$βSEt as the acceptor. Similarly, another 4-O-substituted product than the benzyl-substituted and/or another type of 1-substituted derivatives than the 1-thioethyl substituted product, can be obtained by instead of (4-OBn)GlcNH$_2$βSEt employing another 4-O- and/or 1-substituted acceptor.

Example 12

Synthesis of Fucα1-4(3-OBn)GlcNH$_2$βSEt. The synthesis of this compound is achieved similarly as above, but with an enzyme which gives the α1-4 linked product and with (3-OBn)GlcNH$_2$βSEt as the acceptor. Similarly, another 3-O-substituted product than the bensyl-substituted and/or another type of 1-substituted derivative than the 1-thioethyl substituted product, can be obtained by instead of (3-OBn) GlcNH$_2$βSEt employing another 3-O- and/or 1-substituted acceptor.

Example 13

Synthesis of compounds of the type GlcNAcβ1-3(6-OBn) GlcNH$_2$βSEt, GlcNAcβ1-4(6-OBn)GlcNH$_2$βSEt, GlcNAcβ1-4(3-OBn)GlcNH$_2$βSEt, GlcNAcβ1-3(4-OBn) GlcNH$_2$βSEt, GlcNAcβ1-3(6-OBn)GalNH$_2$βSEt, GlcNAcβ1-4(6-OBn)GalNH$_2$βSEt, GlcNAcβ1-4(3-OBn) GalNH$_2$βSEt and GlcNAcβ1-3(4-OBn)GalNH$_2$βSEt as well as other amino-saccharides of the above type substituted in the 1, 3, 4, or 6-positions with other type of groups, including saccharides, mentioned in the description, are obtained by using N-acetyl-β-D-glucosaminidase which gives the desired linkage, and by using as acceptor the proper one of (6-OBn)GlcNH$_2$βSEt, (3-OBn)GlcNH$_2$βSEt, (4-OBn)GlcNH$_2$βSEt, (6-OBn)GalNH$_2$βSEt, (3-OBn) GalNH$_2$βSEt and (4-OBn)GalNH$_2$βSEt as well as other amino-saccharides of the above type substituted in the 1, 3, 4, or 6-positions with other type of groups, including saccharides, mentioned in the description. As glycosyl donor one can use GlcNAc, a glycoside thereof such as the F-β-glycoside or the nitrophenyl-β-glycoside.

Example 14

Synthesis of compounds of the type GalNAcβ1-3(6-OBn) GlcNH$_2$βSEt, GalNAcβ1-4(6-OBn)GlcNH$_2$βSEt, GalNAcβ1-4(3-OBn)GlcNH$_2$βSEt, GalNAcβ1-3(4-OBn) GlcNH$_2$βSEt, GalNAcβ1-3(6-OBn)GalNH$_2$βSEt, GalNAcβ1-4(6-OBn)GalNH$_2$βSEt, GalNAcβ1-4(3-OBn) GalNH$_2$βSEt and GalNAcβ1-3(4-OBn)GalNH$_2$βSEt as well as other amino-saccharides of the above type substituted in the 1, 3, 4, or 6-positions with other type of groups, including saccharides, mentioned in the description, are obtained by using N-acetyl-β-D-galactosaminidase or another proper β-hexosaminidase which gives the desired linkage, and by using as acceptor the proper one of (6-OBn) GlcNH$_2$βSEt, (3-OBn)GlcNH$_2$βSEt, (4-OBn)GlcNH$_2$βSET, (6-OBn)GalNH$_2$βSEt, (3-OBn)GalNH$_2$βSEt and (4-OBn) GlcNH$_2$βSEt as well as other amino-saccharides of the above type substituted in the 1, 3, 4, or 6-positions with other type of groups, including saccharides, mentioned in the description. As glycosyl donor one can use GalNAc, a glycoside thereof such as the F-β-glycoside or the nitrophenyl-β-glycoside.

Example 15

Synthesis of compounds of the type GalNAcα1-3(6-OBn) GlcNH$_2$βSEt, GalNAcα1-4(6-OBn)GlcNH$_2$βSEt, GalNAcα1-4(3-OBn)GlcNH$_2$βSEt, GalNAcα1-3(4-OBn) GlcNH$_2$βSEt, GalNAcα1-3(6-OBn)GalNH$_2$βSEt, GalNAcα1-4(6-OBn)GalNH$_2$βSEt, GalNAcα1-4(3-OBn) GalNH$_2$βSEt and GalNAcα1-3(4-OBn)GalNH$_2$βSEt as well as other amino-saccharides of the above type substituted in the 1, 3, 4, or 6-positions with other type of groups, including saccharides, mentioned in the description, are obtained by using N-acetyl-α-D-galactosaminidase or another proper α-hexosaminidase which gives the desired linkage, and by using an acceptor the proper one of (6-OBn) GlcNH$_2$βSEt, (3-OBn)GlcNH$_2$βSEt, (4-OBn)GlcNH$_2$βSEt, (6-OBn)GalNH$_2$βSEt, (3-OBn)GalNH$_2$βSEt and (4-OBn) GlcNH$_2$βSEt as well as other amino-saccharides of the above type substituted in the 1, 3, 4, or 6-positions with other type of groups, including saccharides, mentioned in the description. As glycosyl donor one can use GalNAc, a glycoside thereof such the F-β-glycoside or nitrophenyl-β-glycoside.

Example 16

Synthesis of compounds of the type Manα1-3(6-OBn)GlcNH$_2$βSEt, Manα-4(6-OBn)GlcNH$_2$βSEt, Manα1-4(3-OBn)GlcNH$_2$βSEt, Manα1-3(4-OBn)GlcNH$_2$βSEt, Manα1-3(6-OBn)GalNH$_2$βSEt, Manα1-4(6-OBn)GalNH$_2$βSEt, Manα1-4(3-OBn)GalNH$_2$βSEt and Manα1-3(4-OBn)GalNH$_2$βSEt as well as other amino-saccharides of the above type substituted in the 1, 3, 4, or 6-positions with other type of groups, including saccharides, mentioned in the description, are obtained by using α-D-mannosidase which gives the desired linkage, and by using as acceptor the proper one of (6-OBn)GlcNH$_2$βSEt, (3-OBn)GlcNH$_2$βSEt, (1-OBn)GlcNH$_2$βSEt, (6-OBn)GalNH$_2$βSEt, (3-OBn)GalNH$_2$βSEt and (4-OBn)GlcNH$_2$βSEt as well as other amino-saccharides of the above type substituted in the 1, 3, 4, or 6-positions with other type of groups, including saccharides, mentioned in the description. As glycosyl donor one can use mannose, a glycoside thereof such as the F-β-glycoside or the nitrophenyl-β-glycoside.

Example 17

Synthesis of compounds of the type Glcβ1-3(6-OBn)GlcNH$_2$βSEt, Glcβ1-4(6-OBn)GlcNH$_2$βSEt, Glcβ1-4(3-OBn)GlcNH$_2$βSEt, Glcβ1-3(4-OBn)GlcNH$_2$βSEt, Glcβ1-3(6-OBn)GalNH$_2$βSEt, Glcβ1-4(6-OBn)GalNH$_2$βSEt, Glcβ1-4(3-OBn)GalNH$_2$βSEt and Glcβ1-3(4-OBn)GalNH$_2$βSEt as well as other amino-saccharides of the above type substituted in the 1, 3, 4, or 6-positions with other type of groups, including saccharides, mentioned in the description, are obtained by using β-D-glucosidase which gives the desired linkage and by using as acceptor the proper one of (6-OBn)GlcNH$_2$βSEt, (3-OBn)GlcNH$_2$βSEt, (4-OBn)GlcNH$_2$βSEt, (6-OBn)GalNH$_2$βSEt, (3-OBn)GalNH$_2$βSEt and (4-OBn)GlcNH$_2$βSEt as well as other amino-saccharides of the above type substituted in the 1, 3, 4, or 6-positions with other type of groups, including saccharides, mentioned in the description. As glycosyl donor one can use mannose, a glycoside thereof such as the F-β-glycoside or the nitrophenyl-β-glycoside.

In examples 13, 14, 15, 16 and 17 above similar isolation procedures as in example 1 may be used.

Other saccharides than those mentioned above are obtained by using other glycosidases, including α- or β-xylosidases, α-sialidases and endoglycosidases, and other glycosyl donors as mentioned in the description.

A few non-limiting examples of the use of the invention for preparation of amino-deoxy-containing trisaccharides and higher saccharides in conjunction with glycosyltransferases are given below. The glycosyltransferases may be used in more or less isolated form, and may be of natural origin or may be obtained by any recombinant techniques. The glycosyl donors for the glycosyl transferases may be nucleotide sugars or modified nucleotide sugars or any type of glycosyl donor which can be used to promote the glycosyltransferase reaction. It is well known that glycosyltransferases can transfer modified and unnatural glycosyl units and di- tri- and higher oligosaccharides to their acceptors and this can also be used in the invention.

Moreover the glycosyl donors for the glycosyltransferase reactions can be produced either separately or in situ in the reaction vessel (by for instance multi-enzyme systems) and this does not limit the scope of the invention. Also, the glycosidase reaction can be either carried out separately or in the same reaction vessel as the glycosyltransferase reaction and third does not limit the scope of the invention. Moreover, either or both of the glycosidase and the glycosyltransferase can be used in soluble form or in immobilized form to any of the materials mentioned in the description.

Example 18

Synthesis of NeuAcα2-3Galβ1-3GlcNH$_2$βSEt. Galβ1-3GlcNH$_2$βSEt is prepared as described above and used directly or after isolation as acceptor for a β-D-galactoside α2-3-sialyltransferase (e.g. EC 2.4.99.4) reaction with a suitable glycosyl donor such as CMP-NeuAc. Similarly, another 1-substituted product than the 1-thioethyl substituted product above can be obtained by instead of GlcNH$_2$βSEt employing another type of 1-substituted acceptor as exemplified in the description.

Example 19

Synthesis of NeuAcα2-3-Galβ1-4GlcNH$_2$βSEt, Galβ1-1GlcNH$_2$βSEt is prepared as described above and used directly or after isolation as acceptor for a β-D-galactoside α2-3-sialyltransferase (e.g. EC 2.4.99.5) reaction with a suitable glycosyl donor such as CMP-NeuAc. Similarly, another 1-substituted product than the 1-thioethyl substituted product above, can be obtained by instead of GlcNH$_2$βSEt employing another type of 1-substituted acceptor as exemplified in the description.

Example 20

Synthesis of NeuAcα2-3Galβ1-4(6-OBn)GlcNH$_2$βSEt. Galβ1-4(6-OBn)GlcNH$_2$βSEt is prepared as described above and used directly or after isolation as acceptor for a β-D-galactoside α2-3-sialyltransferase (e.g. EC 2.4.99.5) reaction with a suitable glycosyl donor such as CMP-NeuAc. Similarly, another 6- and/or 1-substituted product than the 6-O-bensyl and 1-thioethyl substituted product above can be obtained by instead of 6-O-bensyl-GlcNH$_2$βSEt employing another type of 6- and/or 1-substituted acceptor as exemplified in the description.

Example 21

Synthesis of NeuAcα2-3Galβ1-3(4-OBn)GlcNH$_2$βSEt. Galβ1-3(4-OBn)GlcNH$_2$βSEt is prepared as described above and used directly or after isolation as acceptor for a β-D-galactoside α2-3-sialyltransferase (e.g. EC 2.4.99.4) reaction with a suitable glycosyl donor such as CMP-NeuAc. Similarly, another 4- and/or 1-substituted product than the 4-O-bensyl and 1-thioethyl substituted product above, can be obtained by instead of 4-O-bensyl-GlcNH$_2$βSEt employing another type of 4- and/or 1-substituted acceptor as exemplified in the description.

Example 22

Synthesis of NeuAcα2-3Galβ1-4(3-OBn)GlcNH$_2$βSEt. Galβ1-4(3-OBn)GlcNH$_2$βSEt is prepared as described above and used directly or after isolation as acceptor for a β-D-galactoside α2-3-sialyltransferase (e.g. EC 2.4.99.5) reaction with a suitable glycosyl donor such as CMP-NeuAc. Similarly, another 3- and/or 1-substituted product than the 3-O-bensyl and 1-thioethyl substituted product above, can be obtained by instead of 3-O-bensyl-GlcNH$_2$βSEt employing another type if 3- and/or 1-substituted acceptor as exemplified in the description.

Example 23

Synthesis of NeuAcα2-6Galβ1-4GlcNH$_2$βSEt. Galβ1-4GlcNH$_2$βSEt is prepared as described above and used directly or after isolation as acceptor for a β-D-galactoside α2-6-sialyltransferase (e.g. EC 2.4.99.1) reaction with a suitable glycosyl donor such as CMP-NeuAc.

Example 24

Synthesis of Galα1-3Galβ1-4GlcNH$_2$βSEt. Galβ1-4GlcNH$_2$βSEt is prepared as described above and used directly or after isolation as acceptor for a α1-3-D-galactosylatransferase (e.g. EC 2.4.1 151) reaction with a suitable glycosyl donor such as UDP-Gal.

Example 25

Synthesis of Galβ1-4(Fucα1-3) GlcNH$_2$βSEt. Galβ1-4GlcNH$_2$βSEt is prepared as described above and used directly or after isolation as acceptor for a α1-3-fucosyltransferase (e.g. EC 2.4.1.152 or 65) reaction with a suitable glycosyl donor such as GDP-Fuc.

Example 26

Synthesis of Fucα1-2Galβ1-4GlcNH$_2$βSEt. Galβ1-4GlcNH$_2$βSEt is prepared as described above and used directly or after isolation as acceptor for a α1-2-fucosyltransferase (e.g. EC 2.4.1.69) reaction with a suitable glycosyl donor such as GDP-Fuc.

Example 27

Synthesis of Fucα1-2Galβ1-3GlcNH$_2$βSEt. Galβ1-3GlcNH$_2$βSEt is prepared as described above and used directly or after isolation as acceptor for a α1-2-fucosyltransferase (e.g. EC 2.4.1.69) reaction with a suitable glycoyl donor such as GDP-Fuc.

Example 28

Synthesis of NeuAcα2-3Galβ1-3GalNH$_2$βSEt. Galβ1-3GalNH$_2$βSEt is prepared as described above and used directly or after isolation as acceptor for a α2-3-sialytransferase (e.g. EC 2.4.99.4) reaction with a suitable glycosyl donor such as CMP-NeuAc.

Example 29

Synthesis of NeuAcα2-3Galβ1-3(NeuAcα2-6) GalNH$_2$βSEt. NeuAcα2-3Galβ1-3GalNH$_2$βSEt is prepared as described above and used directly or after isolation as acceptor for a α2-6-sialyltransferase (e.g. EC 2.4.99.7) reaction with a suitable glycosyl donor such as CMP-NeuAc.

In the examples 23 to 29 above, other 1-substituted products than the 1-thioethyl substituted products above, can be obtained by instead of GlcNH$_2$βSEt employing another type of 1-substituted acceptor as exemplified in the description.

In the isolation of the compounds herein, precipitation from water may be used if hydrophobic groups are present on the acceptors. Also extraction of the product from a solid crude mixture may be used with a suitable solvent e.g. MeOH. These techniques, precipitation and extraction are complementary to chromatography and a combination of one, two or all three of these techniques may be used for isolation.

The synthesis of N-containing saccharides in accordance with the invention is characterized in that the synthesis takes place vie (A) intermediates of the type below (called type II intermediate below):

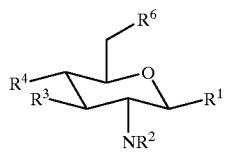

I

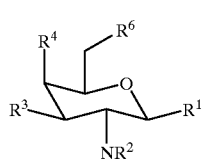

II in which at least one of $R^3$ or $R^4$ is constituted by a hydroxyl group, at least one of $R^3$ or $R^4$ is constituted by an α- or β-glycosidically bound mono-, di-, tri- or higher oligosaccharide unit whose hydroxyl groups or blocked/modified/derivatized with organic and/or inorganic groups (as described herein) and in which $R^1$ is constituted by an O-, S- or C-glycosidically bound organic group or is constituted by an -F or -Cl group ($R^1$ can be bound in α or β configuration). $R^1$ can for example be a methyl, ethyl, other alkyl group (e.g., lower alkyl), or an aromatic group (e.g., phenyl, p-methyloxyphenyl, or nitrophenol group). $R^2$ is an organic or inorganic group and examples of —$NR^2$ groups are azido-(—$N_3$), —NHOH, —$NSO_3$, —NHAc and N-phthalimido groups. $R^6$ is constituted by a modified hydroxyl group modified with an inorganic or organic group such as e.g. a p-methoxybenzyl group, a benzyl or allyl group, a benzoyl group, an acetyl group, a pivaloyl group or another suitable protective group selected for synthesis by an expert in the art.

The invention is further characterized in that the intermediates of the above type are produced in one or several reaction steps from intermediates of the type below (called type I intermediate here and below; e.g., compounds of Examples 1–29 above):

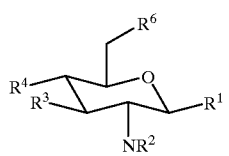

I

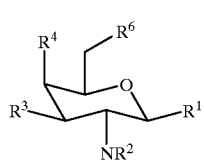

II in which $NR^2$ is constituted by an amino group ($NH_2$ group), at least one of $R^3$ or $R^4$ is constituted by a hydroxyl group, at least one of $R^3$ or $R^4$ is constituted by an α- or β-glycosidically bound mono-, di-, tri or higher oligosaccharide unit whose hydroxyl groups are not blocked/modified/derivatized with organic and/or inorganic groups and in which $R^1$ is constituted by an O-, S- or C-glycosidically bound organic group or is constituted by an —F or —Cl group ($R^1$ can be bound in α or β configuration). $R^6$ is constituted by a hydroxyl group, sulfate group, carboxyl group, phosphate group, a hydroxyl group modified with an organic group such as e.g. a p-methoxybenzyl group, a benzyl or allyl group, a benzoyl group, an acetyl group, a pivaloyl group or another suitable protective group selected for synthesis by an expert in the art.

Non-limiting examples of intermediates of types I and II together with synthesis steps used in the method of the invention are illustrated below:

1994, pp. 206–229 and the references therein; the last-named volume also offers a good general, nonlimiting survey of the structure and applications of biologically active carbohydrates. Thus, acetylation can be achieved by conventional techniques employing acetic anhydride and pyridine, allylation or benzylation employing allyl halide or benzyl halide, respectively. For reviews, see Paulsen, Chem.

TYPE I INTERMEDIATE (S)　　　　　　　　TYPE II INTERMEDIATE (S)

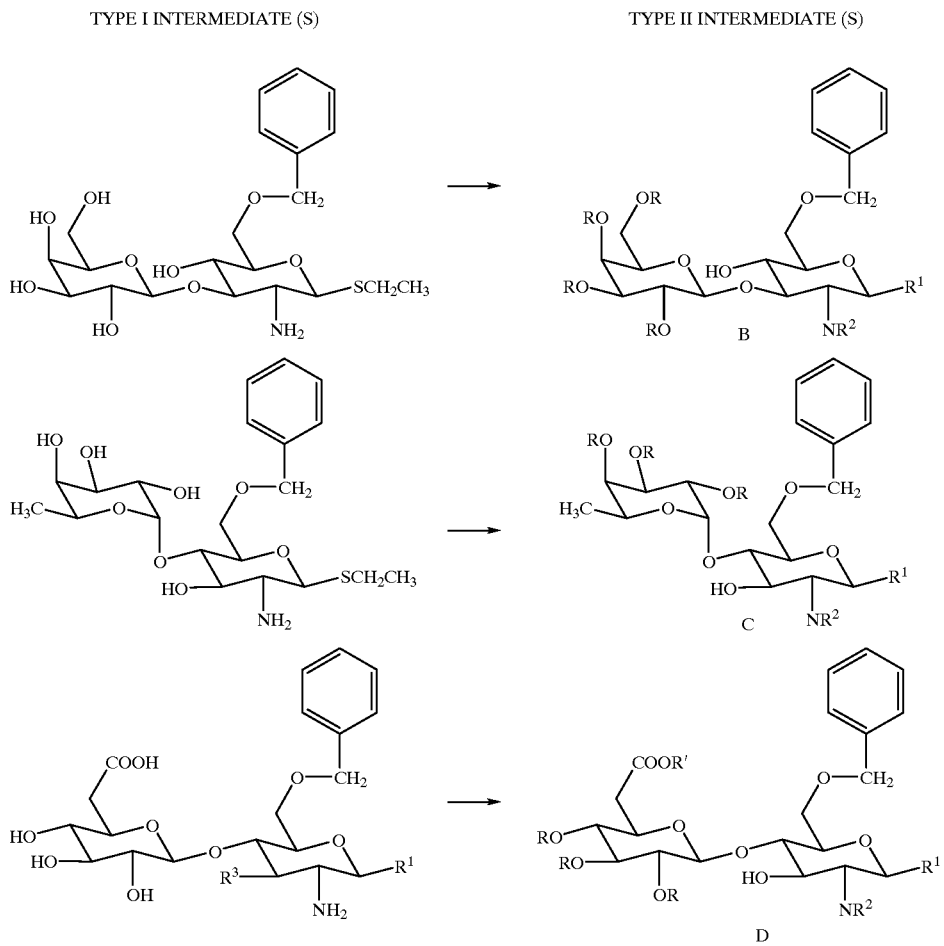

The above examples illustrate the conversion from type I intermediate(s) to type II intermediates in one or several steps. In the examples above $R^1$ is constituted e.g. by a —SEt group (when one step is used for the conversion of intermediate type I to intermediate type II) or by another organic or inorganic group (when at least two steps are used for the conversion from type I intermediate to type II intermediate) and R is constituted by e.g. an ester group such as acetyl, benzoyl, pivaloyl group, for example, or an alkyl or aromatic group such as e.g. allyl, p-methoxybenzyl, benzyl or chlorobenzyl group.

The manner of carrying out the conversion of type I intermediate to type II intermediate does not limit the scope of the invention and suitable reagents and reaction conditions for the desired conversion can be easily selected by an expert in the art of carbohydrate synthesis (for a general overview of carbohydrate synthesis and generally used protective groups for modifying/derivatizing carbohydrates see e.g. Binkley: Modern Carbohydrate Chemistry, Marcel Dekker, New York, 1988 with references and Molecular Glycobiology, edited by Fukuda and Hindsgaul, IRL Press, Soc. Rev., vol. 13, pages 15–45; Khan and Hindsgaul in Molecular Glycobiology, pages 206–229, Fukuda and Hindsgaul, Editors, IRL Press, Oxford. For a reference to the use of thioethyl glycosides in the synthesis of various glycosides or for use as glycosyl donors in convergent block synthesis of tri-, tetra- or larger saccharides, see e.g., references cited in the Khan and Hindsgaul article.

Intermediates of type II can be used for various applications and preferably according to the invention for the synthesis of higher N-containing oligosaccharides or for the synthesis of derivates in which the free hydroxyl group in intermediate II is derivatized with another organic group or an inorganic group. Examples thereof are given in the following illustrations which show the conversion from type I intermediate via type II intermediate (intermediate II is not sketched below) and further to the final product (too arrows are shown in the examples below and represent conversions, usually in three or more steps). These conversions are carried out in a simple manner by an expert in the art with chemical or enzymatic steps (in the present instance with one or more of the enzymes from the groups glycosyl transferases, glycosidases, lipases, peptidases) and do not limit the scope of the invention. —OR groups in the schema below are constituted preferably by —OH groups but one or several of the OR can also be constituted by one or more suitable organic or inorganic groups, e.g. of the type cited in conjunction with the figures above, $R^6$ can be constituted by a hydroxyl group, an inorganic group (sulfate, phosphate, carboxyl, for example), an organic group of aliphatic or aromatic nature, e.g. of the above-named type, $R^3$ or $R^4$ are constituted by an inorganic group e.g. of the above-named type or by an organic group like an α- or β-glycosidically bound mono-, di-, tri- or higher oligosaccharide unit whose hydroxyl groups are not modified/derivatized or are modified/derivatized entirely or in part with organic and/or inorganic groups, $R^1$ is e.g. an —OH group or an O-, S-, C-glycosidically bound, organic group (including a saccharide) such as e.g. an —SEt, —SPhMe group (can be used for block synthesis or the synthesis of other glycosides), an —OMe, —O(CH$_2$)$_n$CH$_3$, —O(CH$_2$)$_n$COOMe, —O amino acid, O peptide group or derivatives thereof, etc., and examples of —NR$^2$ groups are azido-(—N$_3$), —NHOH, —NSO$_3$, —NHAc, NH alkyl and N-phthalimido groups. NR$^2$ may be selected from one of for example (a) HNC(O)R, (b) NPhtalimido, (c) NHR or (d) NRR', where in (a) R symbolizes an aliphatic or aromatic compound; nonlimiting examples of NHC(O)R include N-chloromethoxyacetyl, N-phenoxyacetal, NHBoc, NHAc and NHC(O) (CH$_2$)$_n$CH$_3$ (n is an integer equal to or greater than 1) and where in (c) R symbolizes an aliphatic or aromatic compound; nonlimiting examples of NHR are NH(CH$_2$)$_n$CH$_3$ (n is an integer equal to or greater than 0), and where in (d) R and R' symbolize an aliphatic or aromatic compound; nonlimiting examples of R and R' are —(CH$_2$)$_n$CH$_3$ (n is an integer equal to or greater than 0).

The aglycon of the product obtained according to the invention may no only be used in glycosidation reactions (for formation of other glycosides or for synthesis of oligosaccharide containing the lactosamine sequence) but may also be used for covalent binding to another molecule such as a protein, bead or a solid support and the resulting product may then be used for various purposes. Thus, nitrophenyl glycosides are for example useful after reduction to aminophenyl glycoside for covalent binding to various proteins or solid supports, which then may be used in diagnostic reagents, in down stream processing for separation of various proteins and enzymes including glycosyltransferases with specificity for acceptors containing the saccharide sequence of the invention or for solid phase synthesis of oligosaccharides.

The following can be cited as specific examples of products illustrated below in product type C when —OR and $R^1$ are —OH groups, $R^3$ is a β-glycosidically bound galactopyranosyl group and NR$^2$ is NH$_2$ (Lewis-a). In both these latter examples the protective groups/derivatization were removed after the type II intermediate was reacted with a phycopyranosyl derivative (type II A intermediate with e.g. peracetylated phycopyranose) or a galactopyranosyl derivative (type II C intermediate with e.g. peracetylated galactopyranose). Such syntheses are carried out in a simple manner by an expert in the art and do not limit the scope of the invention. Type I intermediate is synthesized with the aid of e.g. enzymatic technology (is glycosylated as catalyst).

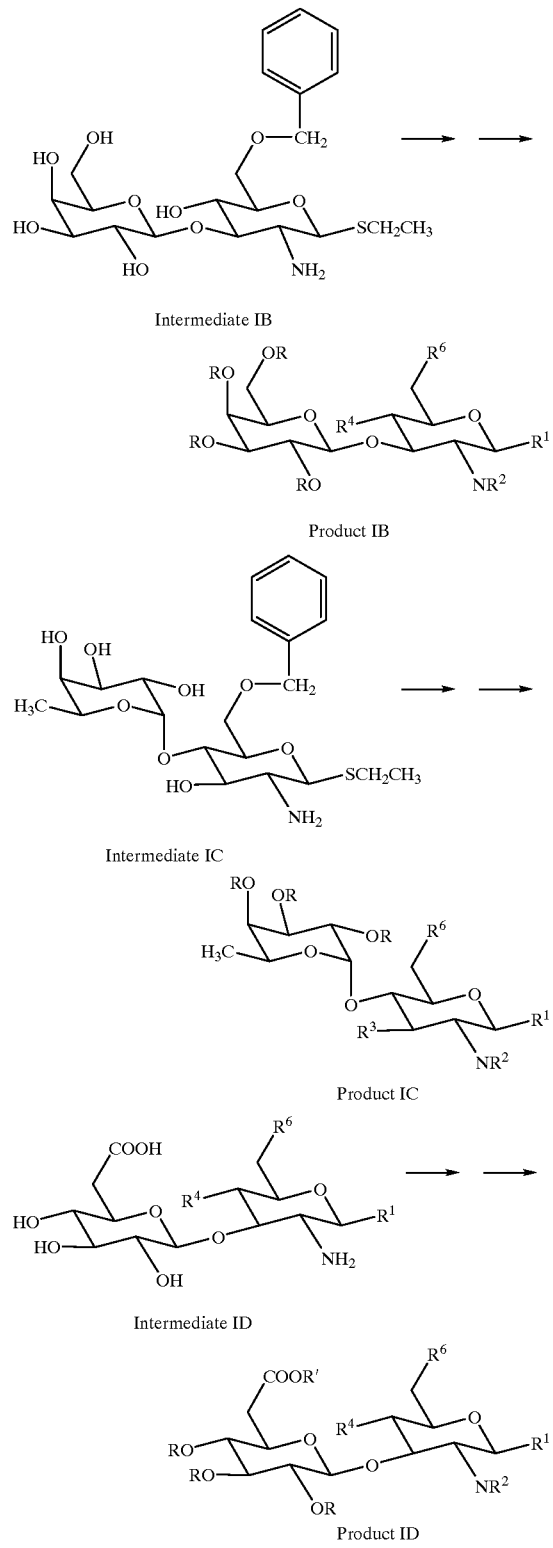

More specifically, product B and C above may be Lewis-a, sialylated Lewis-a, 3'O-sulphated Lewis-a or a derivative thereof. Thus, for example, peracetylation of intermediate IB with acetic anhydride and pyridine gives peracetylated IB in which the 4-OH group of the glucosamine residue is non-modified. Then, reaction with e.g. peracetylated L-fucopyranose gives a peracetylated precursor to product B, which after deacetylation with e.g. catalytic amounts of NaOMe, gives the thioethyl derivative of Lewis-a (i.e. product B in the scheme above in which $R^1$ represents —SEt, $R^2$ represents an acetyl group, $R^4$ represents an α-linked L-fucopyranosyl group and R=H. Moreover, for example, peracetylation of intermediate IC with acetic anhydride and pyridine gives peracetylated IC in which the 3-OH group of the glucosamine residue is non-modified. Then, reaction of with e.g. peracetylated D-galactopyranose gives a peracetylated precursor to product C, which after deacetylation with e.g. catalytic amounts of NaOMe, gives the thioethyl derivative of Lewis-a (i.e. product C in the scheme above in which $R^1$ represents —SEt, $R^2$ represents an acetyl group, $R^3$ represents a β-linked D-galactopyranosyl group and R=H). The skilled in the art may use other derivatives e.g. benzyl or chloro benzyl of intermediates IB and IC and other derivatives of fucose or galactose, respectively, in order to obtain other derivatives of Lewis-a and/or higher yields. Other monosaccharides than fucose or galactose may be used similarly to obtain other trisaccharides than the Lewis-a determinant. The thioethyl group may be used by the skilled in the art for several purposes and may thus be removed or used for introduction of other aglycons (e.g. selected from those mentioned above) or for convergent block synthesis of higher saccharides. Intermediate IB may also first be selectively modified in the galactosyl part by a chemical or enzymatic reaction. The skilled in the art can select a reaction leading to the 3'-O-sulphated-derivatives e.g. of intermediate IB or product B or C, which in the latter case thus gives 3'-O-sulpho-Lewis-a or a derivative thereof (for specific sulphation of carbohydrates see e.g. Tetrahedron Lett. (1994) pp. 6563–6).

Intermediates I, II or product obtained according to the invention may also be converted by enzymatic methods using e.g. lipases, sulphatases, glycosyltransferases and oxidases. In this way hydroxyl groups may be selectively modified with e.g. acyl groups, sulphate groups, saccharide groups, carboxyl groups and other organic groups respectively, thus further extending the utility of the products and method of the invention for preparation of different derivatives and higher saccharides. Specific examples are the selection of a suitable intermediate or product according to invention for reaction with e.g. a glycosyltransferase (EC 2.4) such as a galactosyl, glycosyl-, galactosylaminyl-, glucosaminyl-, mannosyl-, xylosyl-, or a sialyltransferase or a sulphatase to obtain e.g. a specifically glycosylated or a sulphated compound from an intermediate or product according to the invention.

Several glycosyltransferases (belonging to EC group 2.4) such as (Galβ1-3GalNAc)α2-3sialyltransferase and (Galβ1-3/4GlcNAc)α1-3/4fucosyltransferase can transfer sialyl groups and fucosyl groups, respectively, to different types of disaccharide amino derivatives modified in the 2-N-position. (Definitions: Sialyl, here abbreviated NeuAc, is used here as an abbreviation for structures of sialic acid and analogs of sialic acid which are transferred by sialyltransferase and fucosyl, here abbreviated Fuc, is used here as an abbreviation for structures of L-fucopyranose and analogs of L-fucopyranose which are transferred by fucosyltransferase).

Thus, a suitable intermediate according to the invention may be selected (or as obtained after chemical or enzymatic conversion of a hydroxyl group) by the skilled in the art to use as an acceptor with β2-3sialyltransferase as catalyst and a suitable CMP-NeuAc as glycosyl donor to obtain the corresponding α2-3sialylated product.

Similarly, a suitable intermediate may be selected with α1-3fucosyltransferase as catalyst and a suitable GDP-Fuc as glycosyl donor by the skilled in the art to obtain the corresponding α-fucosylated product.

Moreover, a lipase may be selected by the skilled in the art for partial acylation of a specific hydroxyl group.

Also, a combination of the two glycosyltransferase reactions may be selected by the skilled in the art and used to obtain e.g. NeuAcα2-3Galβ1-3(Fucα1-3)GlcNR$^2$R$^1$.

The above derivatives can then be converted to other derivatives (e.g. by chemical modification of the R groups as described above, or by further enzymatic reactions. The above saccharides and derivatives may be used in the various types of applications described above as appropriate. Examples are in clinical, diagnostic, downstream processing applications.

The intermediates and products obtained with the method according to the invention may be used directly for biological applications or may be used for further synthesis to obtain various products employing enzymatic and/or chemical methods of interest for e.g. various clinical, diagnostic, downstream processing or for food supplement purposes.

Typical Preparation of Galβ1-3(6-OBn)GlcNH$_2$βSet (Intermediate IB above)

The following type of reaction was used for preparative synthesis of the title compound with β-galactosidase from bovine testes as the catalyst:

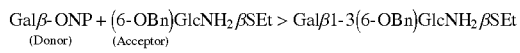

Conditions: Donor (0.15 M; ONP=o-nitrophenyl group) and acceptor (0.1M) were dissolved in sodium phosphate buffer, 50 mM, and the pH was adjusted to 6.8. The β-galactosidase preparation (ammonium sulphate precipitate) was added at 35° C. and the reaction allowed to proceed for 65 h. The reaction mixture was heated to 80° C. (5 min), allowed to cool and the precipitate separated by brief centrifugation. The pH of the mixture was corrected (2 M NaOH) to 10 and extracted with ethyl acetate which removed practically all of the starting material together with part of the product and donor. The water phase was diluted three times with water and applied on SP-Sepharose Fast Flow and eluted with sodium acetate (2.5 mM, pH 4.5) and a gradient of sodium chloride (0–0.2 M). The product containing fractions were evaporated and dissolved in MeOH, evaporated and subjected to a second ion-exchange chromatographic step as above. The product and acceptor containing fractions were adjusted to pH 11, evaporated, dissolved in 99.5% ethanol and recrystalized which gave pure product.

Typical Preparation of GlcAβ1-3(6-OBn)GlcNH$_2$βSEt (Intermediate ID above:

The following type of reaction was used for preparative synthesis of the title compound with β-glucuronidase from E. coli as the catalyst:

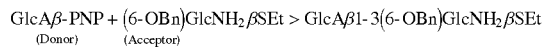

Conditions: Donor (4 g; PNP=p-nitrophenyl group) and acceptor (6 g) were dissolved in 215 ml of sodium acetate buffer, 50 mM, and the pH was adjusted to 6.3. The β-glucuronidase preparation (0.3 g; E. coli; Sigma, St. Louis) was added and the reaction allowed to proceed for 11 h at 30° C. when ca 50% (2 g) of the donor had reacted as judged by liberated p-nitrophenol. The reaction mixture was heat treated, extracted by EtOAc and purification by Q-Sepharose (Pharmacia, Uppsala) was used employing sodium acetate (2.5 mM, pH 11) and a gradient of sodium chloride (0–0.2 M) instead.

Typical Preparation of GlcNAcβ1-3(6-OBn)GlcNH$_2$βSEt and GalNAcβ1-3(6-OBn)GlcNH$_2$βSEt The following type of reaction was used for preparative synthesis of the title compounds with the β-N-acetyl-D-hexosaminidase from *Asperigillus oryzae* (80% ammonium sulphate precipitate) as the catalyst:

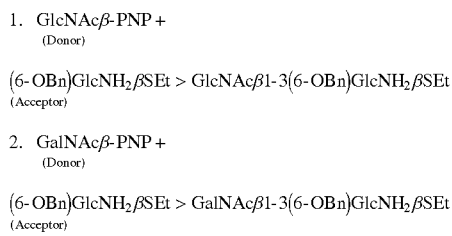

Conditions: Donor (PNP=p-nitrophenyl group) and acceptor were dissolved in sodium phosphate buffer, 20 mM, and pH was adjusted to 7.0 (GlcNAc-PNP) or 6.0 (GalNAc-PNP). The enzyme preparation was added and the reaction proceeded at room temperature until ca 37 mM (GlcNAc-PNP) and 27 mM (GalNAc-PNP) of the donor had reacted. The products were isolated with an extraction-ion exchange isolation procedure (with ethanol and SP-ion-exchanger).

Typical Preparation of Fucα1-4(6-OBn)GlcNH$_2$βSEt (Intermediate IC)

This compound was prepared using a bovine kidney or bovine testes preparation (e.g. ammonium sulphate preparations) and isolated using e.g. extraction and ion-exchange chromatography (SP-Sepharose) principally as described above.

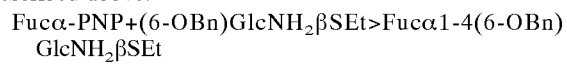

Amino-saccharides, where an —OH group in the saccharide exchanged for an —NH$_2$ group, in several cases have a higher (or modified) biological activity than the corresponding hydroxyl- or N-acetylamino-deoxy-saccharides, e.g. in the binding to selectins important for the initiation of inflammation processes (binding of leucocytes to epithelial cells in blood vessels). The opportunity to use such saccharides therapeutically, e.g. in acute or chronic inflammatory conditions (e.g. reperfusion, injury, and septic shock) is investigated. An important component in this and in other cases is the selective synthesis of di- and oligosaccharides in sufficient quantities. The present invention describes a novel technique for synthesis of amino-saccharides.

Amino-deoxy-di-, tri- or higher oligosaccharides which contain one or more amino —NH$_2$ groups are of high interest for food, agricultural, pharmaceutical or diagnostic applications of carbohydrates, to modify the metabolism of the substance and/or to increase the biological effect of the natural substance.

About ten different monosaccharides are included in the carbohydrate part of the glycoconjugates: D-glucose (Glc), D-galactose (Gal), N-acetyl-D-glucosamine (GlcNAc), N-acetyl-D-neuraminic acid (NeuSAc), D-mannose (Man), L-fucose (Fuc), N-acetyl-D-galactosamine (GalNAc), xylose (Xyl), and arabinose (Ara) (the abbreviations in brackets are according to IUPAC-IUB's abridged terminology for monosaccharides, J.Biol.Chem. (1982), vol. 257, pages 3347–3354, in which publication one also can find the nomenclature used in this text to describe oligosaccharide sequences). The number of possible structures will be almost infinitely great because both the anomeric configuration and the position of the O-glycosidic bond can be varied.

The organic chemical techniques used today for synthesis of these oligosaccharide structures require an extensive protective group chemistry with many steps of synthesis and expensive catalysts (see e.g. Binkley: Modern Carbohydrate Chemistry, Marcel Dekker, New York, 1988, with references). Low total yields are obtained in these complicated reaction schemes and the technique is not favorable, especially for larger scale work.

Selective chemical synthesis of amino group containing carbohydrates and derivatives require advanced protection group chemistry with many synthetic steps. (see e.g. Binkley: Modern Carbohydrate Chemistry, Marcel Dekker, New York, 1988, with references). Efficient techniques for preparation of such carbohydrates and derivatives thereof are thus desired.

Further variations and modifications of the foregoing will be apparent to those skilled in the art and such variations and modifications are attended to be encompassed by the claims that are appended hereto.

Swedish Priority Application 9301677-2 filed on May 17, 1993 is relied on and incorporated by reference.

U.S. Pat. No. 5,246,840; U.S. Pat. No. 4,918,009; U.S. Pat. No. 4,415,665; U.S. patent application Ser. No. 07/834,575, filed on Feb. 18, 1992, now U.S. Pat. No. 5,372,937; and U.S. patent application Ser. No. 07/940,866, filed on Oct. 29, 1992, now abandoned, are incorporated by reference in their entirety (especially for their teachings concerning acceptor substances, donor substances, and enzymes). WO 93/03168 (PCT/SE92/00541) is incorporated by reference in its entirety (especially for its teachings concerning acceptor substances, donor substances, and enzymes).

U.S. patent application Ser. No. 08/190,162, filed on Apr. 6, 1994, now U.S. Pat. No. 5,532,147 is incorporated by reference in its entirety (especially for its teachings concerning organic or inorganic groups).

What is claimed is:

1. A method of producing an amino-deoxy di- or oligosaccharide compound which either consists of or is a fragment or analog of a carbohydrate part in a glycoconjugate, said method comprising (1) reacting
      (a) at least one donor substance comprising a mono, di- or oligosaccharide, a glycoside or a derivative thereof,
      (b) at least one acceptor substance comprising an amino-deoxy mono-, di-, or oligosaccharide, or glycoside thereof, and
      (c) an E.C. group 3.2 glycosidase or a modified 3.2 glycosidase to form an amino-deoxy di- or oligosaccharide compound,
      wherein said glycosidase is a recombinant glycosidase, and
   (2) optionally isolating said amino-deoxy di- or oligosaccharide compound.

2. The amino-deoxy di- or oligosaccharide compound which either consists of or is a fragment or analog of a carbohydrate part in a glycoconjugate, prepared by the method according to claim 1, provided that when said donor substance is galactosyl or sialyl 2-3 galactosyl and when said acceptor substance is 2-amino-2-deoxyglucopyranosyl then a β1–4 linkage cannot contain

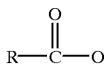

or NHR, and provided that said donor substance is not an (amino) monosaccharide.

3. An amino-deoxy di- or oligosaccharide which either consists of or is a fragment or analog of a carbohydrate part in a glycoconjugate, having a formula I or II

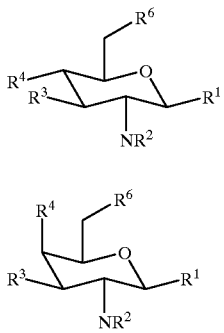

in which I is a derivatized 2-amino-2-deoxy-D-glucopyranoside and II is a derivatized 2-amino-2-deoxy-D-galactopyranoside and at least one of $R^1$, $R^3$, $R^4$, and $R^6$ is a hydroxyl group or an organic or an inorganic group and $R^2$ is —$H_2$, an organic group or an inorganic group and in which at least one of $R^3$, $R^4$, or $R^6$ is a mono-, di-, tri- or higher oligosaccharide group which is glycosidically bound to a remaining part of I or II and a remainder of $R^1$, $R^3$, $R^4$ and $R^6$ is non-derivatized or is derivatized with one or more organic or inorganic groups, provided that when said donor substance is galactosyl or sialyl 2-3 galactosyl and when said acceptor substance is 2-amino-2-deoxyglucopyranosyl then a β1–4 linkage cannot contain

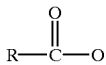

or NHR, and provided that said donor substance is not an (amino) monosaccharide.

4. The amino-deoxy di- or oligosaccharide defined in claim 3, wherein each of $R^1$, $R^3$, $R^4$, and $R^6$ is a member selected from the group consisting of hydroxyl group, aliphatic group, aromatic group, saccharide group, sulphate group, carboxyl group, and phosphate group wherein at least one of $R^1$, $R^3$, $R^4$, or $R^6$ is a mono-, di-, tri- or higher oligosaccharide group which is glycosidically bound to I or II and the remainder of $R^1$, $R^3$, $R^4$ and $R^6$ is non-derivatized or is derivatized with one or more groups selected from the group consisting of hydroxyl group, aliphatic group, aromatic group, saccharide group, sulphate group, carboxyl group, and phosphate group, and wherein $NR^2$ is $NH_2$ or NHAc.

5. The method as defined in claim 1, wherein said amino-deoxy-monosaccharide is 2-amino-2-deoxy-D-glucopyranose, 2-amino-2-deoxy-D-galactopyranose, 2-amino-2-deoxy-D-mannopyranose; or a 2-amino-2-deoxy-D-glucopyranoside, a 2-amino-2-deoxy-D-galactopyranoside, or a 2-amino-2-deoxy-D-mannopyranoside selected from the group consisting of:

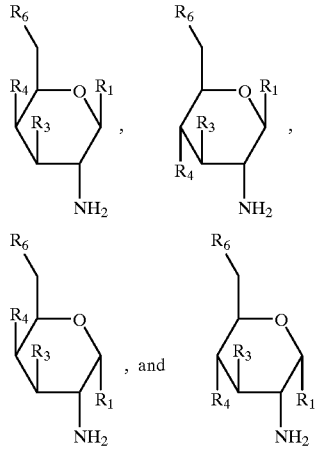

wherein $R_3$, $R_4$, and $R_6$ are —OH; and $R_1$ is pentenyl-, —SEt, —SPh, OetBr, —OEtSiMe$_3$, —OAll, —OPh, —OCH$_2$Ph, or —OR, wherein R is $CH_3(CH_2)_n$ and n is 0–12, or wherein R is an amino acid or peptide.

6. The method as defined in claim 5, wherein said monosaccharide is a derivatized monosaccharide.

7. The method as defined in claim 1, wherein said amino-deoxy mono-, di-, or oligosaccharide, is derivatized.

8. The method as defined in claim 7, wherein said derivative group replaces one or two of the hydroxyl groups of the positions 2, 3, 4, 5 or 6 of said amino-deoxy mono-, di-, or oligosaccharide and wherein said derivative group is a member selected from the group consisting of allyloxy-(CH$_2$=CH—CH$_2$O—), benzyloxy-(PhCH$_2$O—), benzoyloxy-(PhCOO—), chloroacetyloxy-(ClCH$_2$COO—), p-methoxybenzyloxy-(p-MeO-PhCH$_2$O—), trityl-(Ph$_3$CO—), trialkylsilyloxy-, tosylate-, mesylate-, phosphate-, sulfate-, carboxylate, pivaloyl-group, tetrahydropyranyl, (2-methoxyethoxy) methylisopropylidene ketal, cyclohexylidene ketal, benzylidene acetal, orthoester, —ONO$_3$, sulfate-, phosphate-, carboxylate, —OC(O)R, and RCOO— where R is $CH_3(CH_2)_n$ and where n=1–20, and a pivaloyloxy-group, or where two vicinal hydroxyl groups have been replaced with a benzylidene acetal, isopropylidene ketal or an ortho ester.

9. An amino-deoxy di- or oligosaccharide compound which either consists of or is a fragment or analog of a carbohydrate part in a glycoconjugate, represented by the formula D—O-(amino-)saccharide wherein D is a monosaccharide, disaccharide or oligosaccharide residue which is α or β O-glycosidically linked to the (amino)saccharide, said (amino)saccharide is a 2-amino-2-deoxy-glucopyranoside, 2-amino-2-deoxy-galactopyranoside, or 2-amino-2-deoxy-mannopyranoside selected from the group consisting of:

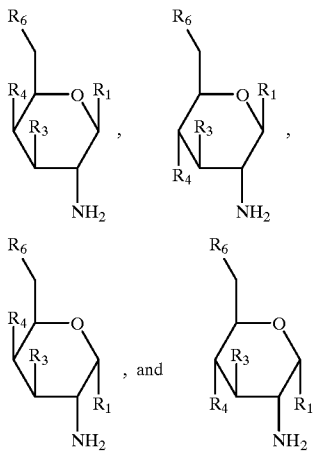

where $R_3$, $R_4$, and $R_6$ are —OH and $R_1$ is pentenyl-, —SEt, —SPh, OEtBr, —OEtSiMe$_3$, —OAll, —OPh, —OCH$_2$Ph, or —OR where R is CH$_3$(CH$_2$)$_n$ where n is 0–12 or where R is an amino acid or peptide, provided that when said donor substance is galactosyl or sialyl 2-3 galactosyl and when said acceptor substance is 2-amino-2-deoxyglucopyranosyl then a β1–4 linkage cannot contain

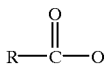

or NHR, and provided that said donor substance is not an (amino) monosaccharide.

10. The method as defined in claim 1 wherein said di- or oligosaccharide produced by said method is a type I intermediate having the formula I or II

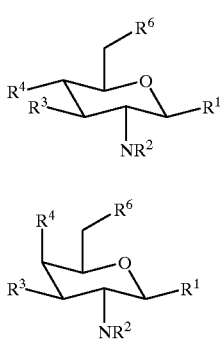

wherein $R^1$ is an O-, S-, or C-glycosidically bound organic group, or an —F or —Cl group, wherein NR$^2$ is an amino group, wherein at least one of $R^3$ or $R^4$ is a hydroxyl group and at least one of $R^3$ or $R^4$ is a glycosidically-bound mono-, di-, or oligosaccharide unit having hydroxyl groups that are not blocked, modified, or derivatized with organic and/or inorganic groups, and wherein $R^6$ is a hydroxyl group, a sulfate group, a carboxyl group, a phosphate group, or a modified hydroxyl group.

11. The method as defined in claim 10 further comprising modifying said type I intermediate to a type II intermediate having the formula III or IV

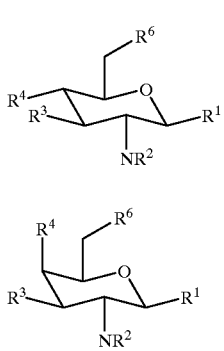

wherein $R^1$ is an O-, S-, or C-glycosidically bound organic group, or an —F or —Cl group, wherein $R^2$ is an organic or inorganic group, at least one of $R^3$ or $R^4$ is a hydroxyl group and at least one of $R^3$ or $R^4$ is a glycosidically-bound mono-, di-, or oligosaccharide unit having hydroxyl groups that are blocked, modified, or derivatized with at least one organic and/or inorganic group, and wherein $R^6$ is a modified hydroxyl group, modified with an inorganic or organic group.

12. The amino-deoxy di- or oligosaccharide compound prepared by the method according to claim 1 represented by the formula:

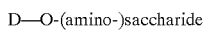

D—O-(amino-)saccharide wherein D is a mono-, di- or oligosaccharide group or an analog thereof, which is α- or β- or O-glycosidically bound to the -(amino-)saccharide, and wherein -(amino-)saccharide is obtained from:

(1) an amino-deoxy mono- or di- or oligosaccharide, or glycoside thereof;

(2) an amino-deoxy-glucopyranoside, an amino-deoxy-galactopyranoside, or an amino-deoxy-mannopyranoside;

(3) a 2-amino-2-deoxy-saccharide substituted in the 3, 4, 5 or 6 OH group with an organic or inorganic group selected from the group consisting of allyloxy- (CH$_2$=CH—CH$_2$O—), benzyloxy-(PhCH$_2$O—), benzoyloxy-(PhCOO—), chloroacetyloxy- (ClCH$_2$COO), p-methoxybenzyloxy-(p-MeO-PhCH$_2$O—), trityl-(Ph$_3$CO—), trialkylsilyloxy-, tosylate-, mesylate-, phosphate-, ONO$_3$, sulfate-, carboxylate, and RCOO— where R is CH$_3$(CH$_2$)$_n$ and where n is 1–20, or where two vicinal hydroxyl groups have been replaced with a benzylidene acetal, isopropylidene ketal or an ortho ester, pivaloyl-group, tetrahydropyranyl, (2-methoxyethoxy)methylisopropylidene ketal, cyclohexylidene ketal, benzylidene acetal, orthoester, benzoyloxy-(PhCOO—); or (4) an amino-deoxy-di-, tri-, or higher oligosaccharide, provided that when said donor substance is galactosyl or sialyl 2-3 galactosyl and when said acceptor substance is 2-amino-2-deoxyglucopyranosyl then a β1–4 linkage cannot contain

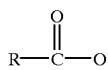

or NHR, and provided that said donor substance is not an (amino) monosaccharide.

13. An amino-deoxy di- or oligosaccharide compound having the formula:

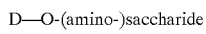

wherein D is a mono-, di- or oligosaccharide group or an analog thereof, which is α- or β- or O-glycosidically bound to the -(amino-)saccharide, and wherein -(amino-)saccharide is obtained from:
(1) an amino-deoxy mono- or di- or oligosaccharide, or glycoside thereof;
(2) an amino-deoxy-glucopyranoside, an amino-deoxy-galactopyranoside, or an amino-deoxy-mannopyranoside;
(3) a 2-amino-2-deoxy-saccharide substituted in the 3, 4, 5 or 6 OH group with an organic or inorganic group selected from the group consisting of allyloxy-($CH_2$=CH—$CH_2$O—), benzyloxy-(PhCH$_2$O—), benzoyloxy-(PhCOO—), chloroacetyloxy-(ClCH$_2$COO), p-methoxybenzyloxy-(p-MeO-PhCH$_2$O—), trityl-(Ph$_3$CO—), trialkylsilyloxy-, tosylate-, mesylate-, phosphate-, ONO$_3$, sulfate-, carboxylate, and RCOO— where R is CH$_3$(CH$_2$)$_n$ and where n is 1–20;
or where two vicinal hydroxyl groups have been replaced with a benzylidene acetal, isopropylidene ketal or an ortho ester, pivaloyl-group, tetrahydropyranyl, (2-methoxyethoxy) methylisopropylidene ketal, cyclohexylidene ketal, benzylidene acetal, orthoester, benzoyloxy-(PhCOO—); or
(4) an amino-deoxy-di, tri-, or higher oligosaccharide, provided that when said donor substance is galactosyl or sialyl 2-3 galactosyl and when said acceptor substance is 2-amino-2-deoxyglucopyranosyl then a β1–4 linkage cannot contain

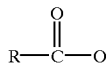

or NHR, and
provided that said donor substance is not an (amino) monosaccharide.

14. An amino-deoxy di- or oligosaccharide compound represented by the formula

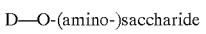

wherein D is a monosaccharide, disaccharide or oligosaccharide residue which is α or β O-glycosidically linked to the (amino)saccharide, said (amino)saccharide is a member selected from the group consisting of

I

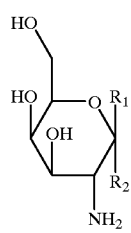

II

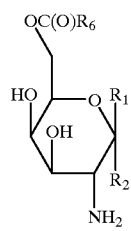

III

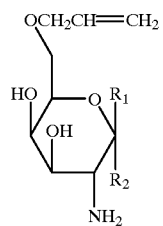

IV

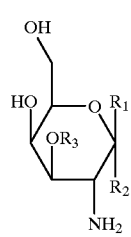

V

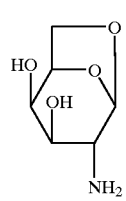

-continued

VI 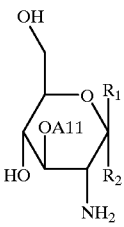

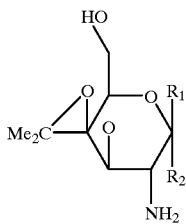

VII

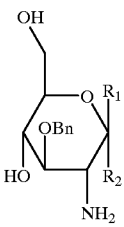

VIII

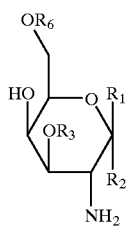

IX

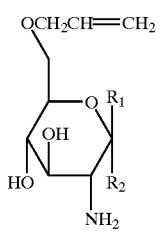

X

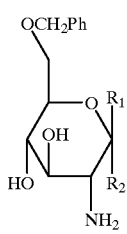

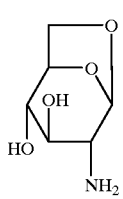

wherein one or two of the hydroxyl groups of the positions 2, 3, 4, 5 or 6 have been replaced with allyloxy- ($CH_2$=CH—$CH_2$O—), benzyloxy-(PhCH$_2$O—), benzoyloxy-(PhCOO—), chloroacetyloxy-(ClCH$_2$COO), p-methoxybenzyloxy-(p-MeO-PhCH$_2$O—), trityl-(Ph$_3$CO—), trialkylsilyloxy-, tosylate-, mesylate-, phosphate-, sulfate-, carboxylate, pivaloyl-group, tetrahydropyranyl, (2-methoxyethoxy) methylisopropylidene ketal, cyclohexylidene ketal, benzylidene acetal, orthoester, —$ONO_3$, sulfate-, phosphate-, carboxylate, —OC(O)R as acetyl-, butanoyl-, octanoyl-, benzoyl, -pivaloyl, and RCOO— where R is $CH_3(CH_2)_n$ and where n=1–20, or a pivaloyloxy-group, or where two vicinal hydroxyl groups have been replaced with a benzylidene acetal, isopropylidene ketal or an ortho ester.

15. The method as claimed in claim 1, wherein said donor substance and said acceptor substance contain one or more of the monosaccharides selected from the group consisting of D-glucose, D-galactose, D-mannose, N-acetylneuraminic acid, N-acetyl-D-galactosamine, N-acetyl-D-glucosamine, L-fucose, xylose, arabinose and analogs thereof.

16. The method as claimed in claim 1, wherein said glycoside in (b) is a glycoside in which the aglycon is glycosidically bound fluoro or is an O-, N-, C-, or S-glycosidically bound aliphatic or aromatic compound.

17. The method according to claim 1 wherein said glycosidase is an endo- or an exoglycosidase or a modified endo- or exoglycosidase.

18. The method according to claim 1 wherein said glycosidase is selected from the group consisting of galactosidase, mannosidase, N-acetyl-hexosaminidase, N-acetyl-glucosaminidase, N-acetyl-galactosaminidase, fucosidase, xylosidase sialidase with α- or β-specificity, and a modified glycosidase thereof.

19. The method as claimed in claim 1 wherein the carbohydrate portion of said donor substance and said acceptor substance comprises one or more of D-galactose, D-mannose, N-acetylneuraminic acid, N-acetyl-D-galactosamine, N-acetyl-D-glucosamine, L-fucose, or analogs thereof.

20. The method as claimed in claim 1 wherein said glycosidase is used in situ or after it has been isolated completely or partly from its natural biological environment.

21. The method according to claim 1 wherein said glycosidase is immobilized via precipitation, adsorption, enclosure, chelation, or covalent bonding, to a polymeric substance or derivative thereof which is insoluble in protic or aprotic solvents.

22. The method according to claim 21, wherein said polymeric substance is a polysaccharide, a plastic, or a glass, and which has been activated and contains reactive groups selected from the group consisting of cyanate, organic sulphonates, aldehyde, diazonium, epoxy, divinylsulphone, and triazine groups.

23. The method according to claim 22, wherein said polysaccharide is cellulose or agarose and said plastic is polyacrylamide, polyvinylalcohol, or polystyrene.

24. An amino-deoxy di- or oligosaccharide compound which either consists of or is a fragment or analog of the carbohydrate part in a glycoconjugate, prepared by a method comprising the steps of
   (1) reacting
      (a) at least one mono-, di- or oligosaccharide, glycoside, or derivative thereof as donor substance,
      (b) at least one acceptor substance comprising an amino-deoxy mono-, di-, oligosaccharide, glycoside or derivative thereof, and
      (c) an E.C. group 3.2 glycosidase to form said aminodeoxy di- or oligosaccharide compound, and
   (2) optionally isolating said amino-deoxy di- or oligosaccharide compound,
   provided that when said donor substance is galactosyl or sialyl 2-3 galactosyl and when said acceptor substance is 2-amino-2-deoxyglucopyranosyl then a β1–4 linkage cannot contain

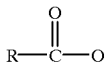

or NHR, and
   provided that said donor substance is not an (amino) monosaccharide.

25. A method of synthesizing an amino-disaccharide, amino-oligosaccharide or a derivative thereof, comprising reacting a monosaccharide, disaccharide, oligosaccharide, glycoside or derivative thereof in the presence of a recombinant glycosidase or a modified glycosidase as catalyst with an amino-deoxy-saccharide or derivative thereof and optionally isolating the amino-saccharide from the product mixture directly or after further chemical/enzymatic modification.

26. A method of producing an amino-deoxy di- or oligosaccharide compound selected from the group consisting of Galβ1-3(6-O-Bn)GlcNH₂βSEt, Fucα1-4(6-O-Bn)GlcNH₂βSEt, Galβ1-4(6-OBn)GlcNH₂βSEt, Galβ1-3GlcNH₂βSEt, Galβ1-3GalNH₂βSEt, Galβ1-4GlcNH₂βSEt, Galβ1-3(6-OAll)GlcNH₂βSEt, Galβ1-4(6-OAll)GlcNH₂βSEt, Galβ1-3(4-OBn)GlcNH₂βSEt, Galβ1-4(3-OBn)GlcNH₂βSEt, Fucα1-4(6-OBn)GlcNH₂βSEt, Fucα1-3(6-OBn)GlcNH₂βSet, Fucα1-3(4-OBn)GlcNH₂βSEt, Fucα1-4(3-OBn)GlcNH₂βSEt, GlcNAcβ1-3(6-OBn)GlcNH₂βSEt, GlcNAcβ1-4(6-OBn)GlcNH₂βSEt, GlcNAcβ1-4(3-OBn)GlcNH₂βSEt, GlcNAcβ1-3(4-OBn)GlcNH₂βSEt, GlcNAcβ1-3(6-OBn)GalNH₂βSEt, GlcNAcβ1-4(6-OBn)GalNH₂βSEt, GlcNAcβ1-4(3-OBn)GalNH₂,βSEt, GlcNAcβ1-3(4-OBn)GalNH₂βSEt, GalNAcβ1-3(6-OBn)GlcNH₂βSEt, GalNAcβ1-4(6-OBn)GlcNH₂βSEt, GalNAcβ1-4(3-OBn)GlcNH₂βSEt, GalNAcβ1-3(4-OBn)GlcNH₂βSEt, GalNAcβ1-3(6-OBn)GalNH₂βSEt, GalNAcβ1-4(6-OBn)GalNH₂βSEt, GalNAcβ1-4(3-OBn)GalNH₂βSEt, GalNAcβ1-3(4-OBn)GalNH₂βSEt, GalNAcα1-3(6-OBn)GlcNH₂βSEt, GalNAcα1-4(6-OBn)GlcNH₂βSEt, GalNAcα1-(3-OBn)GlcNH₂βSEt, GalNAcα1-3(4-OBn)GlcNH₂βSEt, GalNAcα1-3(6-OBn)GalNH₂βSEt, GalNAcα1-4(6-OBn)GalNH₂βSEt, GalNAcα1-4(3-OBn)GalNH₂βSEt, GalNAcα1-3(4-OBn)GalNH₂βSEt, Manα1-3(6-OBn)GlcNH₂βSEt, Manα1-4(6-OBn)GlcNH₂βSEt, Manα1-4(3-OBn)GlcNH₂βSEt, Manα1-3(4-OBn)GlcNH₂βSEt, Manα1-3(6-OBn)GalNH₂βSEt, Manα1-4(6-OBn)GalNH₂βSEt, Manα1-4(3-OBn)GalNH₂βSEt, Manα1-3(4-OBn)GalNH₂βSEt, Glcβ1-3(6-OBn)GlcNH₂βSEt, Glcβ1-4(6-OBn)GlcNH₂βSEt, Glcβ1-4 (3-OBn)GlcNH₂βSEt, Glcβ1-3(4-OBn)GlcNH₂βSEt, Glcβ1-3(6-OBn)GalNH₂βSEt, Glcβ1-4(6-OBn)GalNH₂βSEt, Glcβ1-4(3-OBn)GalNH₂βSEt, Glcβ1-3(4-OBn)GalNH₂βSEt, NeuAcα2-3Galβ1-3GlcNH₂βSEt, NeuAcα2-3Galβ1-4GlcNH₂βSEt, NeuAcα2-3Galβ1-4(6-OBn)GlcNH₂βSEt, NeuAcα2-3Galβ1-3(4-OBn)GlcNH₂βSEt, NeuAcα2-3Galβ1-4(3-OBn)GlcNH₂βSEt, NeuAcα2-6Galβ1-4GlcNH₂βSEt, Galα1-3Galβ1-4GlcNH₂βSEt, Galβ1-4(Fucα1-3)GlcNH₂βSEt, Fucα1-2Galβ1-4GlcNH₂βSEt, Fucα1-2Galβ1-3GlcNH₂βSEt, NeuAcα2-3Galβ1-3GalNH₂βSEt, and NeuAcα2-3Galβ1-3(NeuAcα2-6)GalNH₂βSEt, comprising
   (1) reacting
      (a) at least one donor substance comprising a mono-, di-, or oligosaccharide, a glycoside or a derivative thereof
      (b) at least one acceptor substance comprising an amino-deoxy mono-, di, or oligosaccharide, or glycoside thereof, and
      (c) an E.C. group 3.2 glycosidase or a modified 3.2 glycosidase to form an amino-deoxy di- or oligosaccharide, and compound, wherein said glycosidase is a recombinant glycosidase,
   (2) optionally isolating said amino-deoxy di- or oligosaccharide compound.

27. A method of producing an amino-deoxy di- or oligosaccharide compound selected from the group consisting of Galβ1-3(6-O-Bn)GlcNH₂βSEt, Fucα1-4(6O-Bn)GlcNH₂βSEt, Galβ1-4(6-OBn)GlcNH₂βSEt, Galβ1-3GlcNH₂βSEt, Galβ1-3GalNH₂βSEt, Galβ1-4GlcNH₂βSEt, Galβ1-3(6-OAll)GlcNH₂βSEt, Galβ1-4(6-OAll)GlcNH₂βSEt, Galβ1-3(4-OBn)GlcNH₂βSEt, Galβ1-4(3-OBn)GlcNH₂βSEt, Fucα1-4(6-OBn)GlcNH₂βSEt, Fucα1-3(6-OBn)GlcNH₂βSet, Fucα1-3(4-OBn)GlcNH₂βSEt, Fucα1-4(3-OBn)GlcNH₂βSEt, GlcNAcβ1-3(6-OBn)GlcNH₂βSEt, GlcNAcβ1-4(6-OBn)GlcNH₂βSEt, GlcNAcβ1-4(3-OBn)GlcNH₂βSEt, GlcNAcβ1-3(4-OBn)GlcNH₂βSEt, GlcNAcβ1-3(6-OBn)GalNH₂βSEt, GlcNAcβ1-4(6-OBn)GalNH₂βSEt, GlcNAcβ1-4(3-OBn)GalNH₂,βSEt, GlcNAcβ1-3(4-OBn)GalNH₂βSEt, GalNAcβ1-3(6-OBn)GlcNH₂βSEt, GalNAcβ1-4(6-OBn)GlcNH₂βSEt, GalNAcβ1-4(3-OBn)GlcNH₂βSEt, GalNAcβ1-3(4-OBn)GlcNH₂βSEt, GalNAcβ1-3(6-OBn)GalNH₂βSEt, GalNAcβ1-4(6-OBn)GalNH₂βSEt, GalNAcβ1-4(3-OBn)GalNH₂βSEt, GalNAcβ1-3(4-OBn)GalNH₂βSEt, GalNAcα1-3(6-OBn)GlcNH₂βSEt, GalNAcα1-4(6-OBn)GlcNH₂βSEt, GalNAcα1-(3-OBn)GlcNH₂βSEt, GalNAcα1-3(4-OBn)GlcNH₂βSEt, GalNAcα1-3(6-OBn)GalNH₂βSEt, GalNAcα1-4(6-OBn)GalNH₂βSEt, GalNAcα1-4(3-OBn)GalNH₂βSEt, GalNAcα1-3(4-OBn)GalNH₂βSEt, Manα1-3(6-OBn)GlcNH₂βSEt, Manα1-4(6-OBn)GlcNH₂βSEt, Manα1-4(3OBn)GlcNH₂βSEt, Manα1-3(4-OBn)GlcNH₂βSEt, Manα1-3(6-OBn)GalNH₂βSEt, Manα1-4(6-OBn)GalNH₂βSEt, Manα1-4(3-OBn)GalNH₂βSEt, Manα1-3(4-OBn)GalNH₂βSEt, Glcβ1-3(6-OBn)GlcNH₂βSEt, Glcβ1-4(6-OBn)GlcNH₂βSEt, Glcβ1-4 (3-OBn)GlcNH₂βSEt, Glcβ1-3(4-OBn)GlcNH₂βSEt, Glcβ1-3(6-OBn)

GalNH₂βSEt, Glcβ1-4(6-OBn)GalNH₂βSEt, Glcβ1-4(3-OBn)GalNH₂βSEt, Glcβ1-3(4-OBn)GalNH₂βSEt, NeuAcα2-3Galβ1-3GlcNH₂βSEt, NeuAcα2-3Galβ1-4GlcNH₂βSEt, NeuAcα2-3Galβ1-4(6-OBn)GlcNH₂βSEt, NeuAcα2-3Galβ1-3(4-OBn)GlcNH₂βSEt, NeuAcα2-3Galβ1-4(3-OBn)GlcNH₂βSEt, NeuAcα2-6Galβ1-4GlcNH₂βSEt, Galα1-3Galβ1-4GlcNH₂βSEt, Galβ1-4(Fucα1-3)GlcNH₂βSEt, Fucα1-2Galβ1-4GlcNH₂βSEt, Fucα1-2Galβ1-3GlcNH₂βSEt, NeuAcα2-3Galβ1-3GalNH₂βSEt, and NeuAcα2-3Galβ1-3(NeuAcα2-6)GalNH₂βSEt,
(1) reacting
 (a) at least one mono-, di- or oligosaccharide, glycoside, or derivative thereof as donor substance,
 (b) at least one acceptor substance comprising an amino-deoxy mono-, di-, oligosaccharide, glycoside or derivative thereof, and
 (c) an E.C. group 3.2 glycosidase to form said aminodeoxy di- or oligosaccharide compound, and
(2) optionally isolating said amino-deoxy di- or oligosaccharide compound.

28. The method as defined in claim 1, wherein said amino-deoxy di- or oligosaccharide produced by said process has a formula I or II

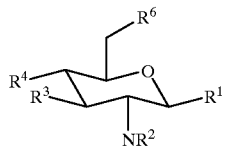

I

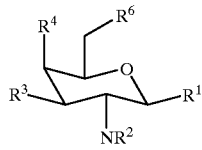

II in which I is a derivatized 2-amino-2-deoxy-D-glucopyranoside and II is a derivatized 2-amino-2-deoxy-D-galactopyranoside and at least one of $R^1$, $R^3$, $R^4$, and $R^6$ is a hydroxyl group or an organic or an inorganic group and $R^2$ is a $H_2$, an organic group or an inorganic group and in which at least one of $R^3$, $R^4$, or $R^6$ is a mono-, di-, tri- or higher oligosaccharide group which is glycosidically bound to a remaining part of I or II and a remainder of $R^1$, $R^3$, $R^4$, and $R^6$ is non-derivatized or is derivatized with one or more organic or inorganic groups.

29. The di- or oligosaccharide produced by the method according to claim 28, provided that when said donor substance is galactosyl or sialyl 2-3 galactosyl and when said acceptor substance is 2-amino-2-deoxyglucopyranosyl then a β1–4 linkage cannot contain

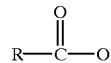

or NHR, and provided that said donor substance is not an (amino) monosaccharide.

30. An amino-deoxy di- or oligosaccharide compound which either consists of or is a fragment or analog of a carbohydrate part in a glycoconjugate, produced by a method comprising
(1) reacting
 (a) at least one donor substance comprising a mono-, di- or oligosaccharide, a glycoside or a derivative thereof,
 (b) at least one acceptor substance comprising an amino-deoxy mono-, di-, or oligosaccharide, or glycoside thereof, and
 (c) an E.C. group 3.2 glycosidase or a modified 3.2 glycosidase to form an amino-deoxy di- or oligosaccharide compound,
(2) optionally isolating said amino-deoxy di- or oligosaccharide compound,
provided that when said donor substance is galactosyl or sialyl 2-3 galactosyl and when said acceptor substance is 2-amino-2-deoxyglucopyranosyl then a β1–4 linkage cannot contain

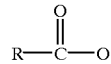

or NHR, and provided that said donor substance is not an (amino) monosaccharide.

31. The method as defined in claim 8,
wherein —OC(O)R is selected from the group consisting of acetyl-, butanoyl-, octanoyl-, benzoyl-, and pivaloyl.

32. The method as defined in claim 1
wherein said recombinant glycosidase has at least 70% homology with a 3.2 glycosidase.

* * * * *